(12) United States Patent
Lee et al.

(10) Patent No.: US 11,266,747 B2
(45) Date of Patent: Mar. 8, 2022

(54) ORALLY ADMINISTERED NANOPARTICLES FOR GENE DELIVERY AND PHARMACEUTICAL COMPOSITION CONTAINING SAME

(71) Applicant: KB Biomed Inc., Chungcheongbuk-do (KR)

(72) Inventors: Yong-Kyu Lee, Chungcheongbuk-do (KR); Dong Yun Lee, Seoul (KR); Sung Hun Kang, Chungcheongbuk-do (KR); Revuri Vishnu, Chungcheongbuk-do (KR)

(73) Assignee: KB BIOMED INC., Chungcheongbuk-Do (KR)

( * ) Notice: Subject to any disclaimer, the term of this patent is extended or adjusted under 35 U.S.C. 154(b) by 578 days.

(21) Appl. No.: 16/096,753

(22) PCT Filed: Apr. 26, 2017

(86) PCT No.: PCT/KR2017/004456
§ 371 (c)(1),
(2) Date: Oct. 26, 2018

(87) PCT Pub. No.: WO2017/188731
PCT Pub. Date: Nov. 2, 2017

(65) Prior Publication Data
US 2019/0111156 A1     Apr. 18, 2019

(30) Foreign Application Priority Data
Apr. 26, 2016  (KR) .......................... 10-2016-0050955

(51) Int. Cl.
*A61K 48/00* (2006.01)
*A61P 3/10* (2006.01)
(Continued)

(52) U.S. Cl.
CPC ............ *A61K 48/0041* (2013.01); *A61K 9/00* (2013.01); *A61K 47/12* (2013.01); *A61K 47/28* (2013.01);
(Continued)

(58) Field of Classification Search
None
See application file for complete search history.

(56) References Cited

U.S. PATENT DOCUMENTS

| 5,424,286 A | 6/1995 | Eng |
| 2003/0124196 A1 | 7/2003 | Weinbach et al. |

(Continued)

FOREIGN PATENT DOCUMENTS

| KR | 1020100122405 A | 11/2010 |
| KR | 10-2011-0061881 A | 6/2011 |

(Continued)

OTHER PUBLICATIONS

Lee et al., Preparation of chitosan self-aggregates as a gene delivery system (J Cont Release, 1998, 51:213-220) (Year: 1998).*

(Continued)

*Primary Examiner* — Arthur S Leonard
(74) *Attorney, Agent, or Firm* — DLA Piper LLP US

(57) ABSTRACT

The present invention relates to a nanoparticle for oral gene delivery, which is a novel oral gene delivery system capable of regulating blood glucose levels in biological systems and insulin secretion in response to ingested meals. More specifically, the present invention relates to a nanoparticle for gene delivery, comprising: an ionic polymer conjugated with bile acid or a bile acid derivative; and a gene; and to a pharmaceutical composition comprising the same.

10 Claims, 16 Drawing Sheets

Specification includes a Sequence Listing.

(51) Int. Cl.
  *A61K 47/12* (2006.01)
  *A61K 47/50* (2017.01)
  *A61K 9/00* (2006.01)
  *A61K 47/28* (2006.01)

(52) U.S. Cl.
  CPC .............. *A61K 47/50* (2017.08); *A61K 48/00* (2013.01); *A61K 48/0075* (2013.01); *A61P 3/10* (2018.01)

(56) References Cited

U.S. PATENT DOCUMENTS

| | | | |
|---|---|---|---|
| 2004/0014698 A1* | 1/2004 | Hortelano | A61K 48/0041 |
| | | | 514/44 R |
| 2005/0196443 A1 | 9/2005 | Weinbach et al. | |
| 2011/0256217 A1 | 10/2011 | Weinbach et al. | |
| 2013/0095187 A1 | 4/2013 | Hahn et al. | |
| 2013/0210717 A1 | 8/2013 | Merzouki | |
| 2015/0147276 A1 | 5/2015 | Ingber et al. | |
| 2017/0065724 A1 | 3/2017 | Lee | |
| 2017/0095566 A1* | 4/2017 | Hanes | A61K 9/0034 |
| 2017/0296481 A1 | 10/2017 | Bae et al. | |
| 2019/0247313 A1 | 8/2019 | Bae et al. | |

FOREIGN PATENT DOCUMENTS

| | | | | |
|---|---|---|---|---|
| KR | 20140091133 A | | 7/2014 | |
| WO | 03017940 A2 | | 3/2003 | |
| WO | 2010131907 A2 | | 11/2010 | |
| WO | 2013138930 A1 | | 9/2013 | |
| WO | 2013185032 A1 | | 12/2013 | |
| WO | WO-2014084421 A | * | 6/2014 | ......... A61K 49/0423 |
| WO | 2014133351 A1 | | 9/2014 | |
| WO | 2016070082 A1 | | 5/2016 | |

OTHER PUBLICATIONS

Jean et al., Effective and safe gene-based delivery of GLP-1 using chitosan/plasmid-DNA therapeutic nanocomplexes in an animal model of type 2 diabetes (Gene Ther, 2011, 18:807-816) (Year: 2011).*

Katun et al. Oral delivery of taurocholic acid linked heparin-docetaxel conjugates for cancer therapy (J Cont Rei, 2013, 170:74-82) (Year: 2013).*

Jean et al., "Chitosan-based therapeutic nanoparticles for combination gene therapy and gene silencing of in vitro cell lines relevant to type 2 diabetes", European Journal of Pharmaceutical Sciences, 45(1):138-149 (2012).

Extended European Search Report in International Application No. 17789915.0-1120 / 3449944, dated Dec. 3, 2019, 7 pages.

* cited by examiner

[FIG. 1]
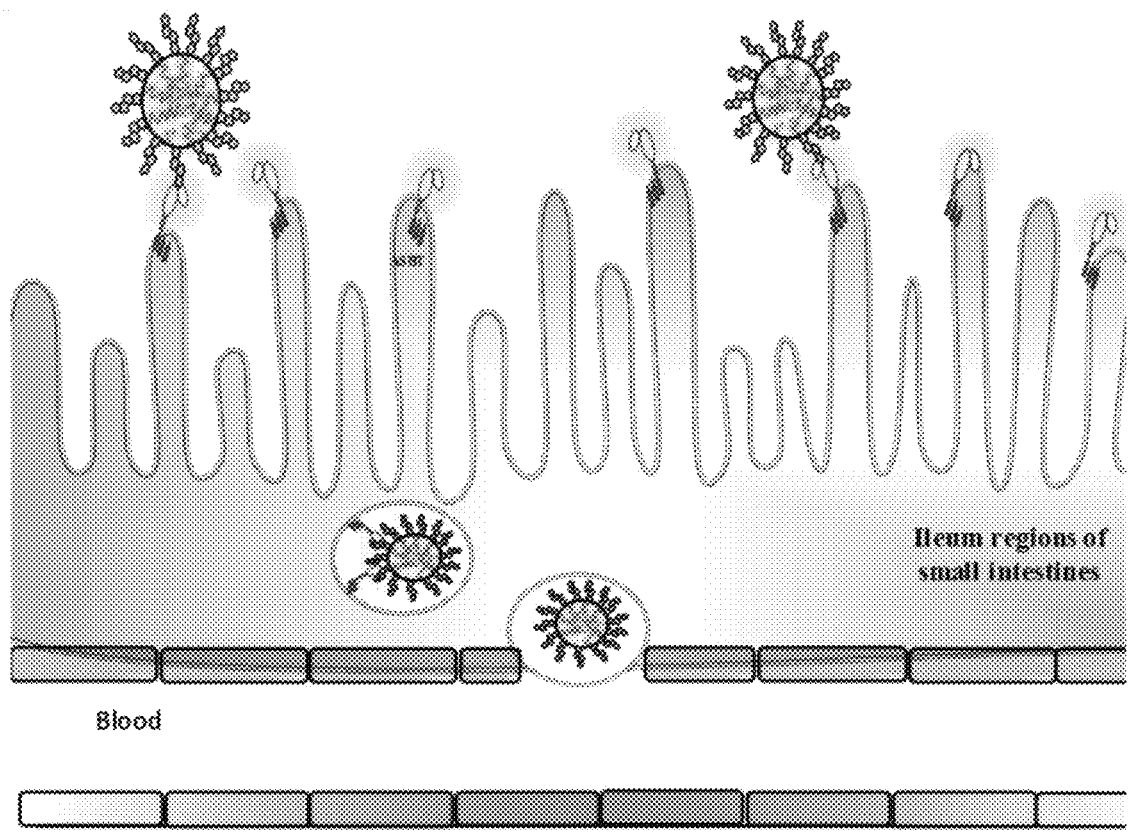

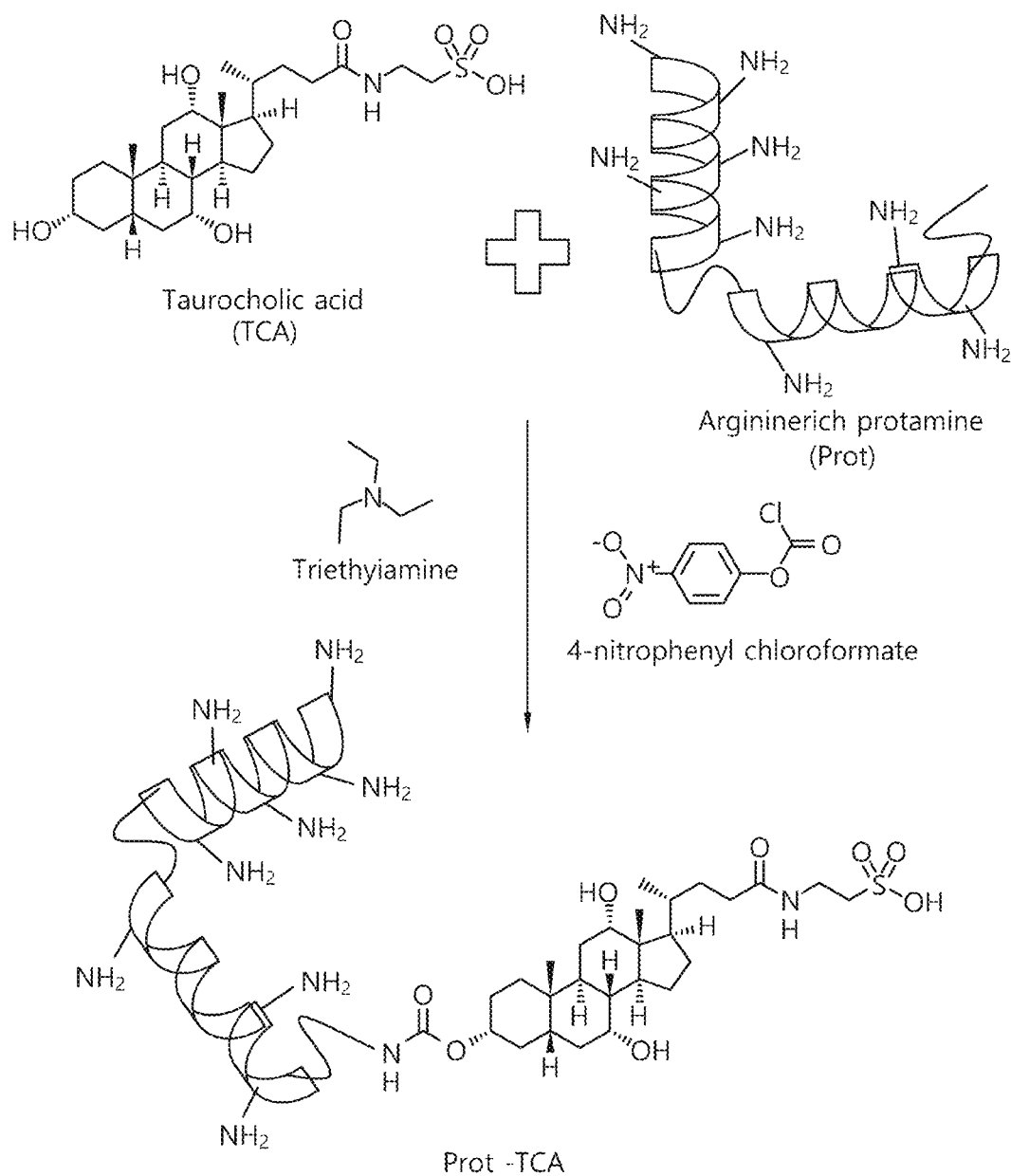
[FIG. 2]

[FIG. 3]
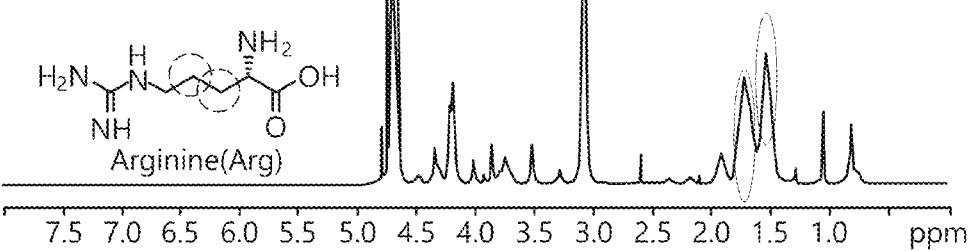
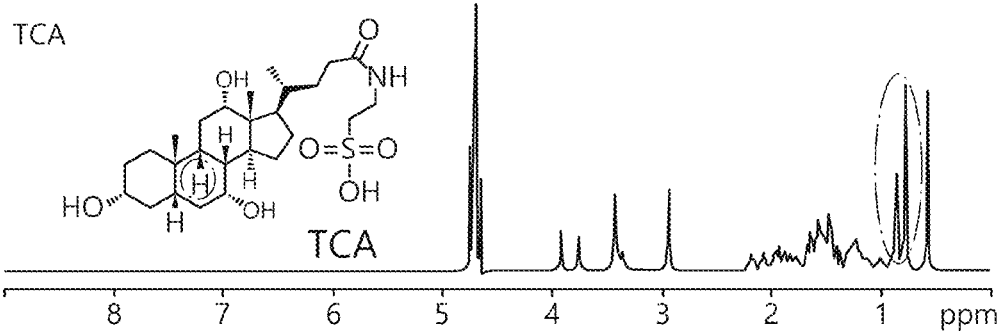
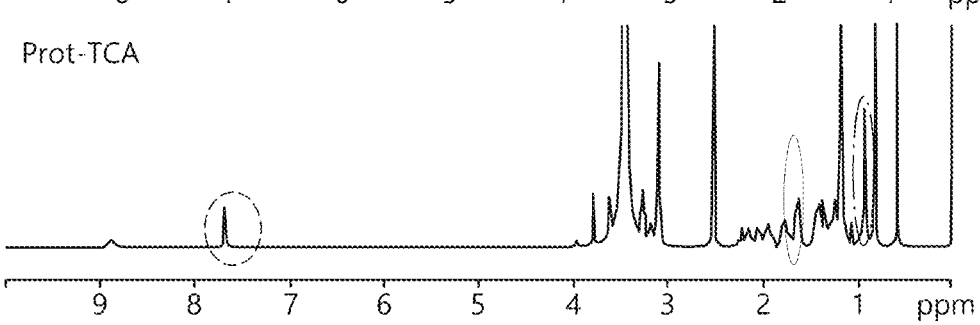
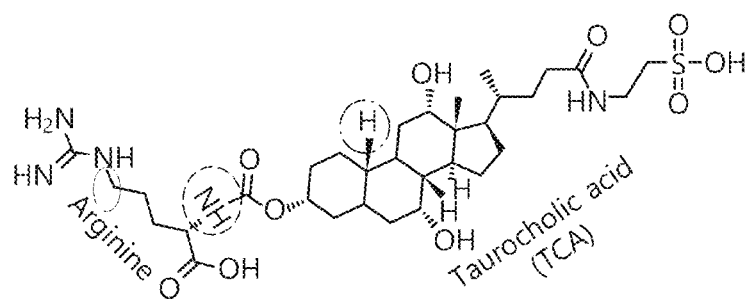
Prot-TCA

[FIG. 4]
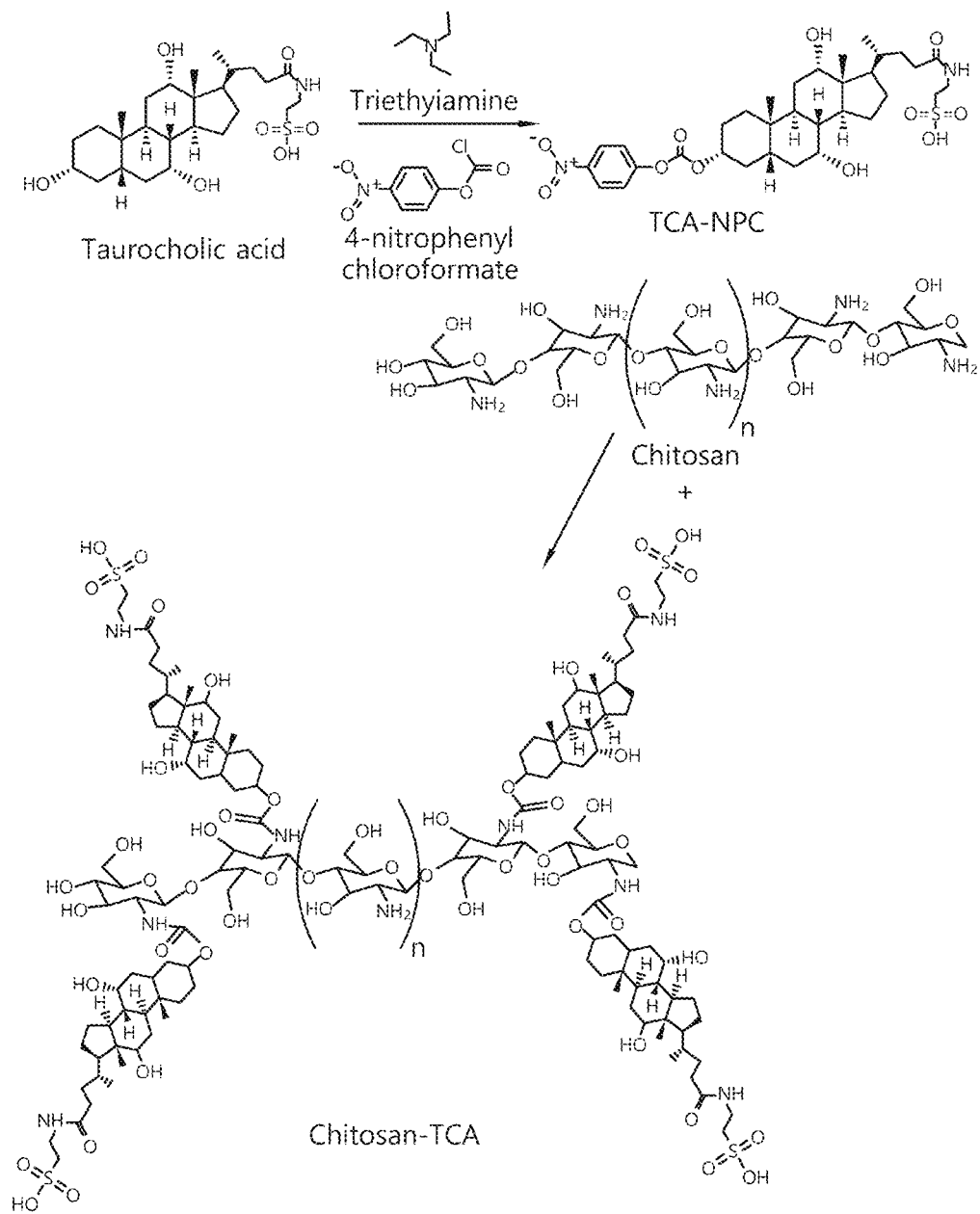

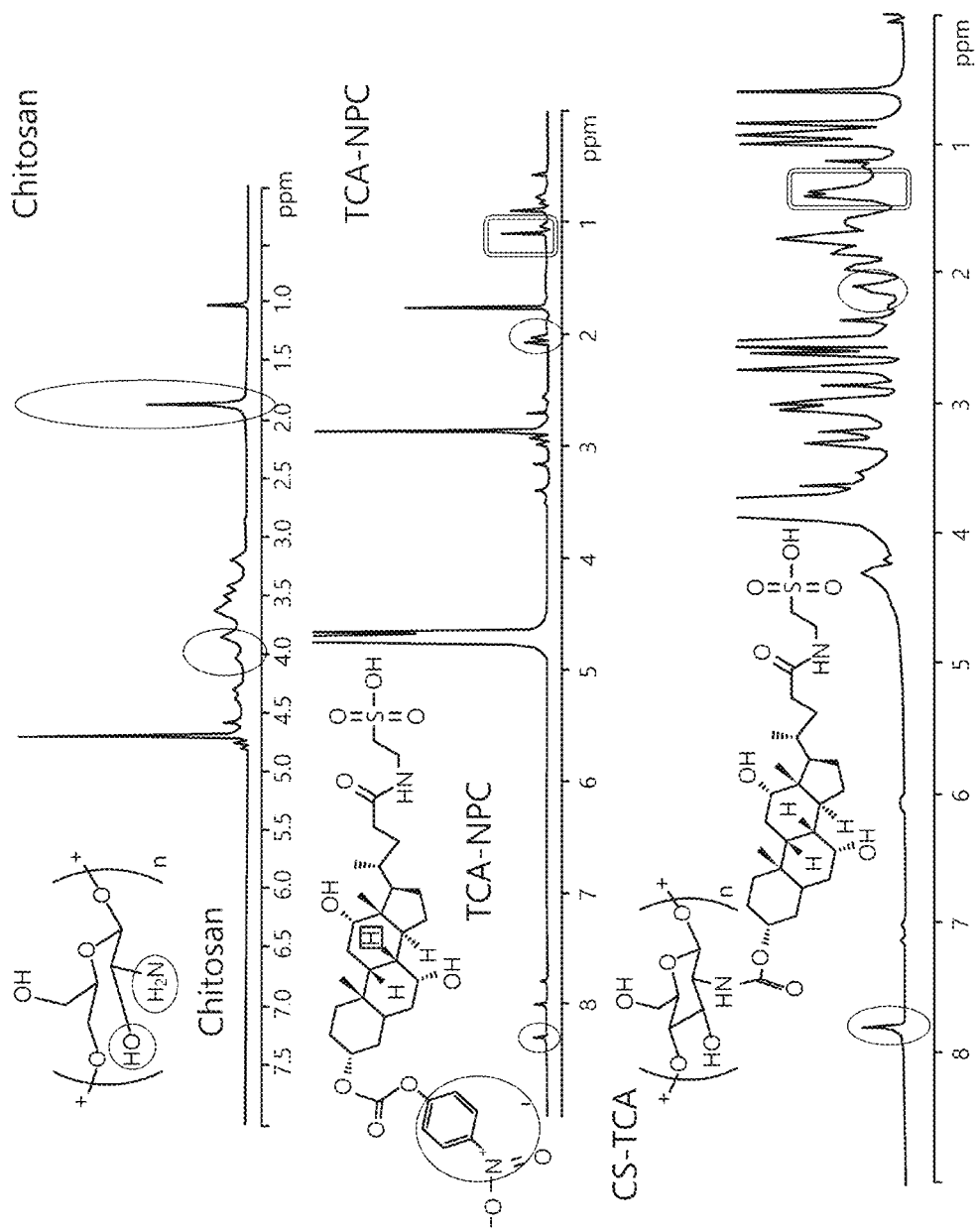
[FIG. 5]

[FIG. 6]
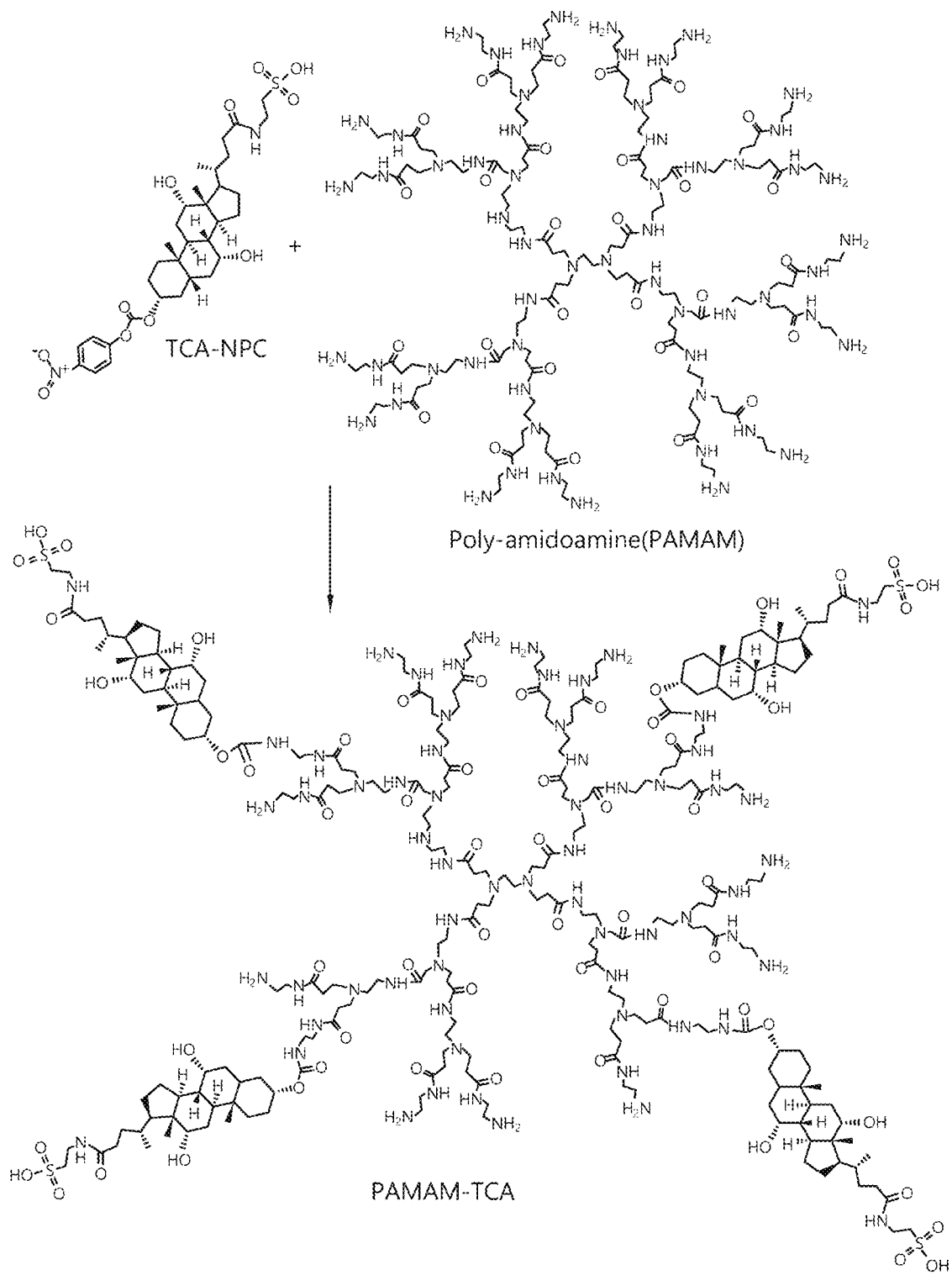

[FIG. 7]
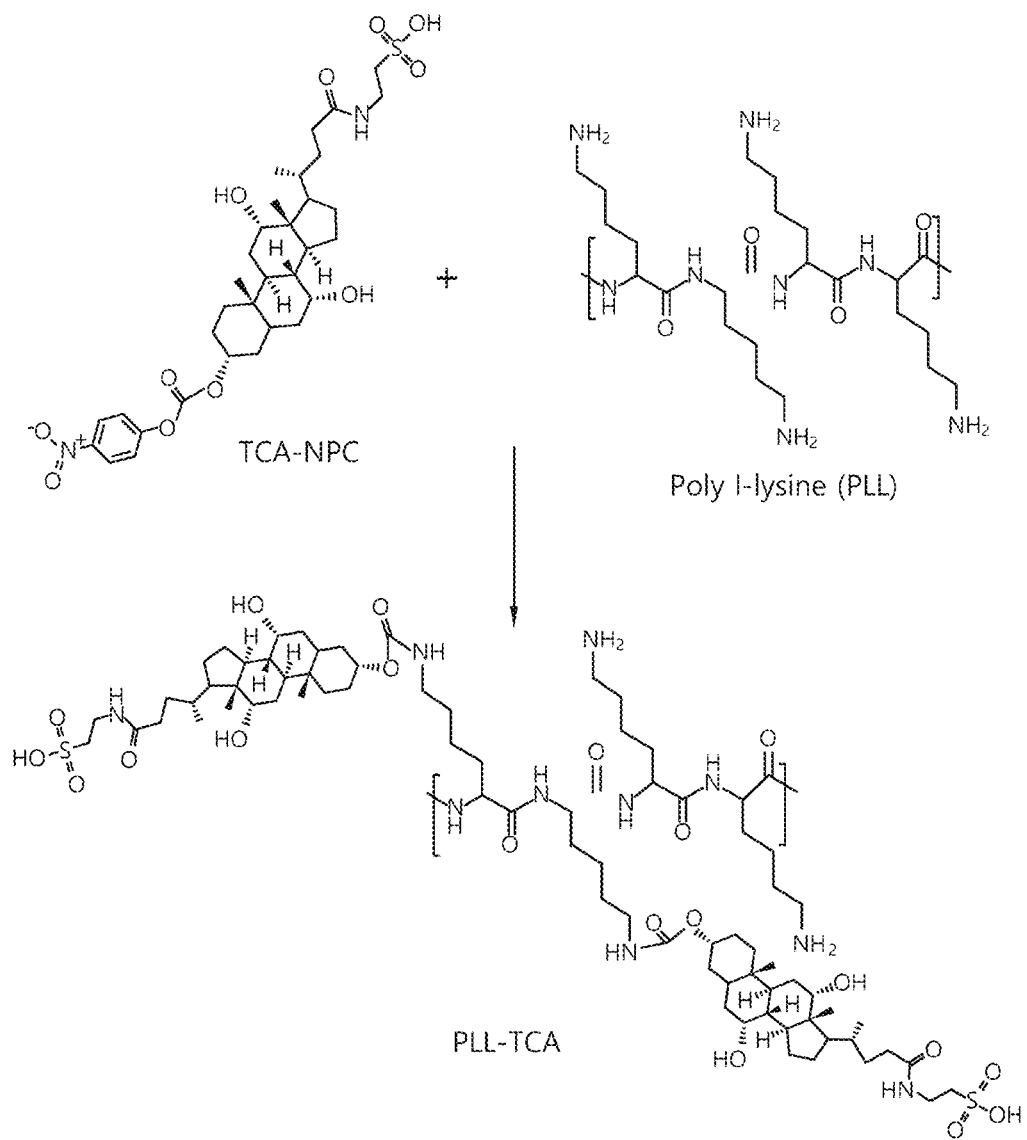

[FIG. 8]
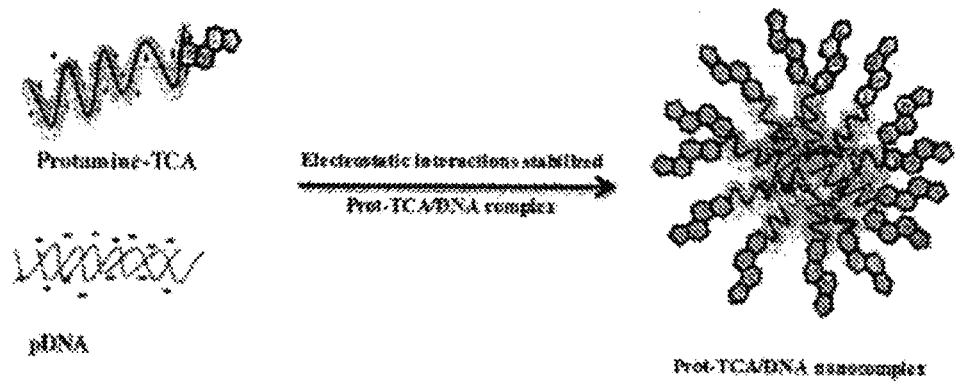
[FIG. 9]
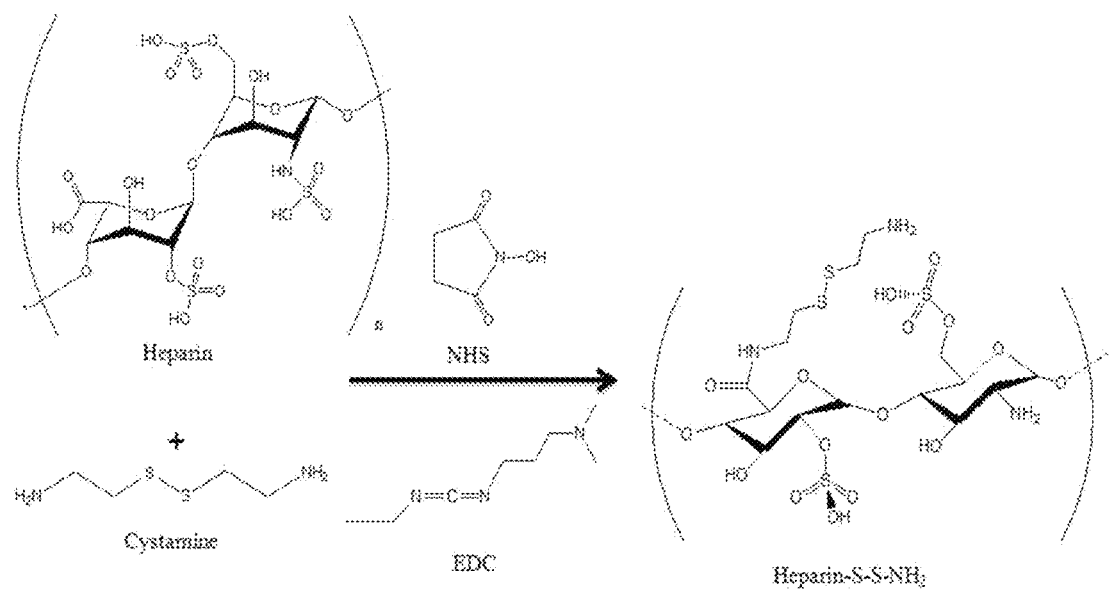
[FIG. 10]
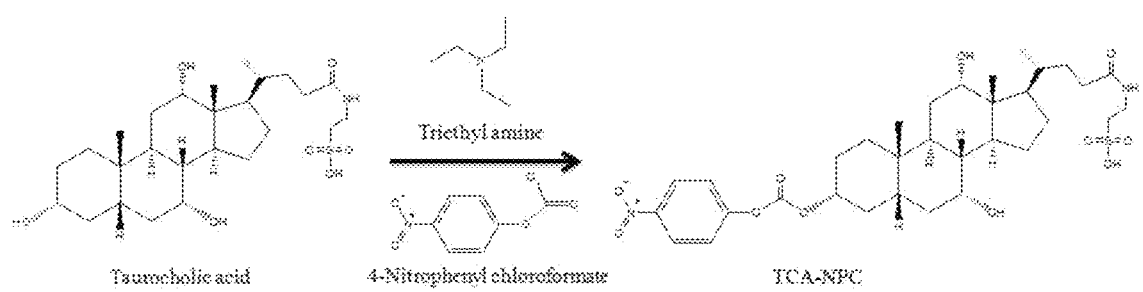

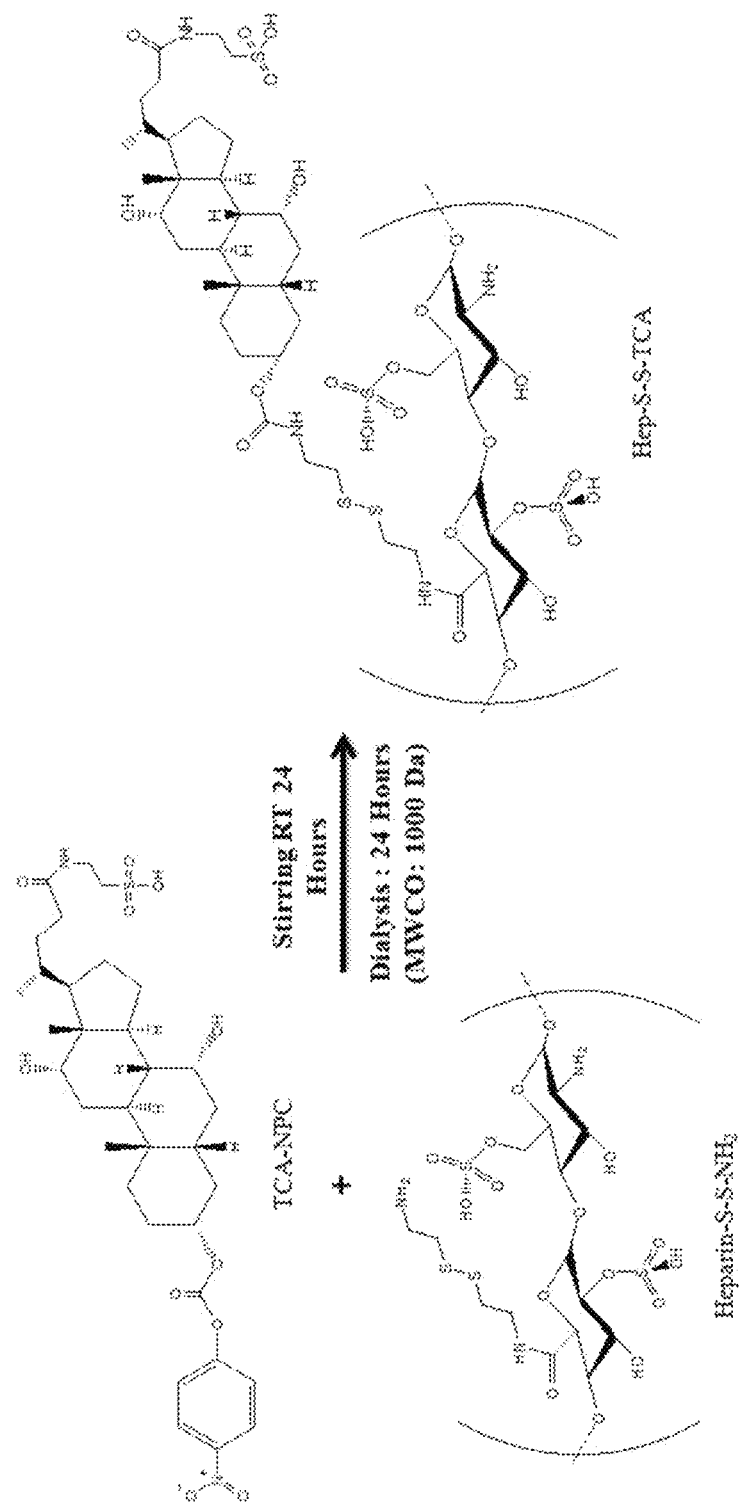
[FIG. 11]

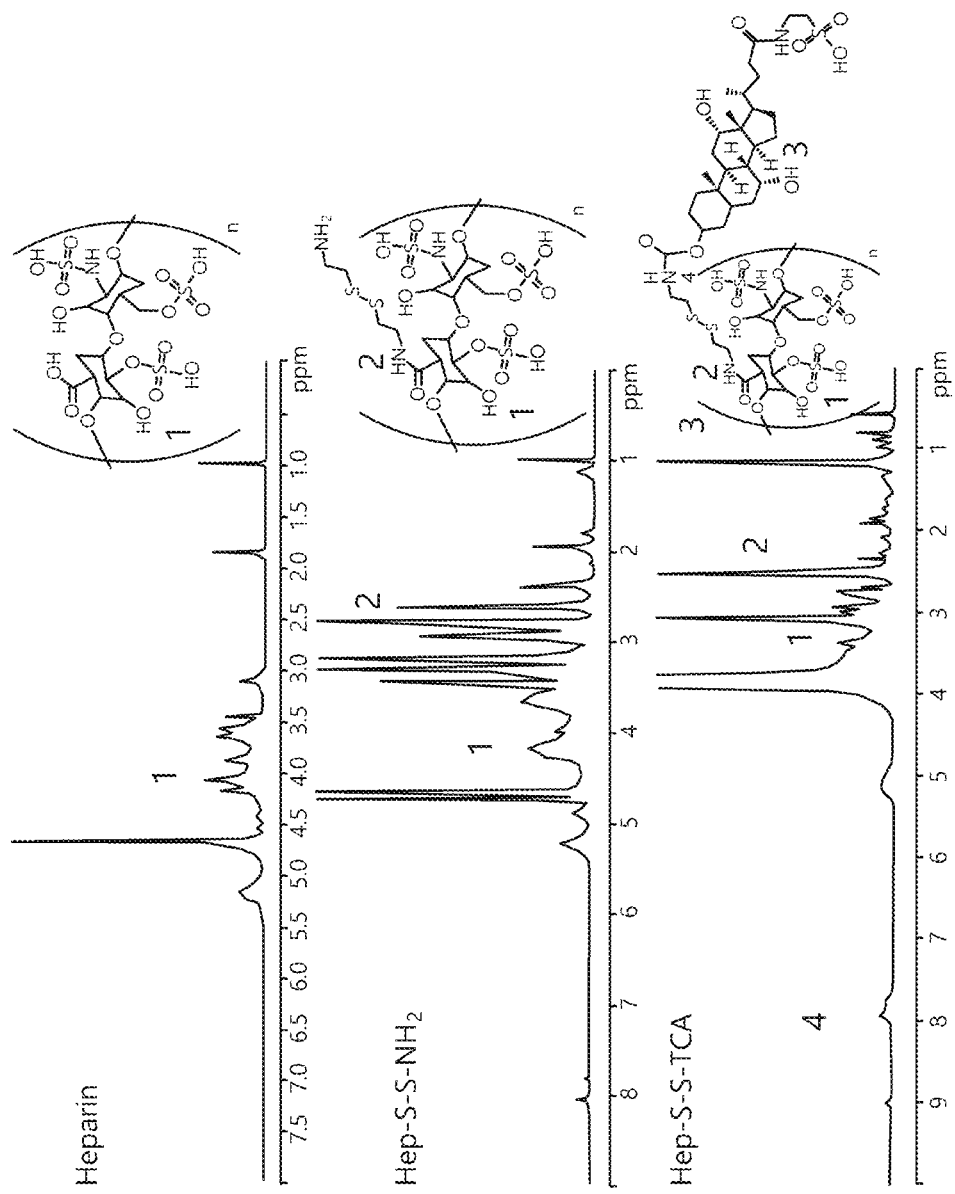
[FIG. 12]

[FIG. 13]
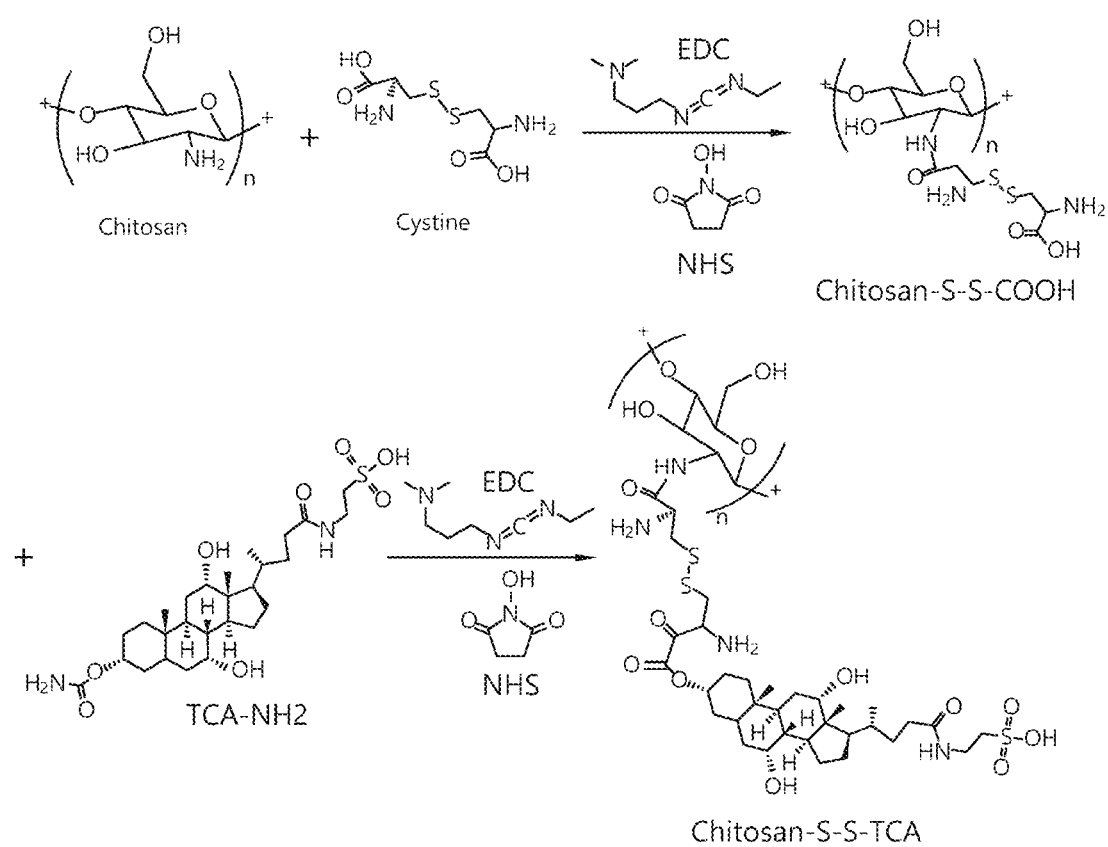

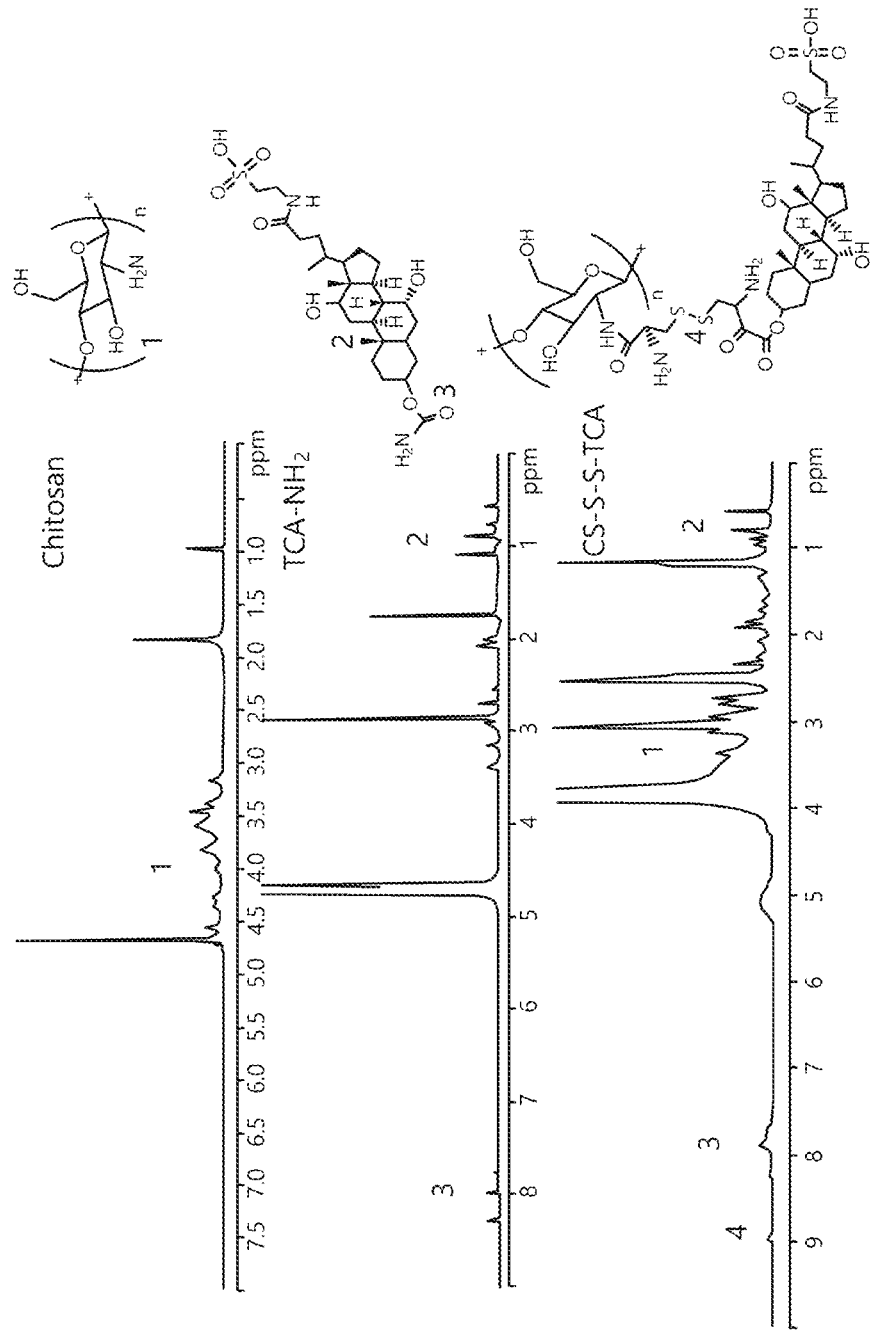
[FIG. 14]

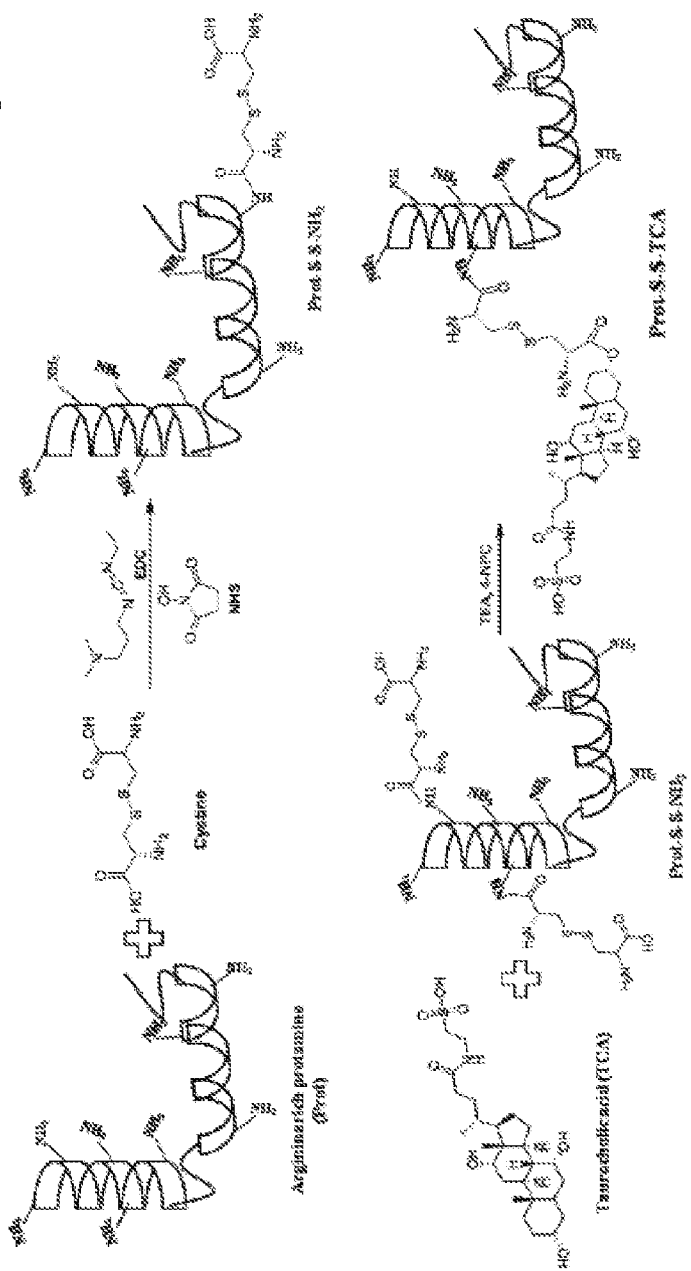
[FIG. 15]

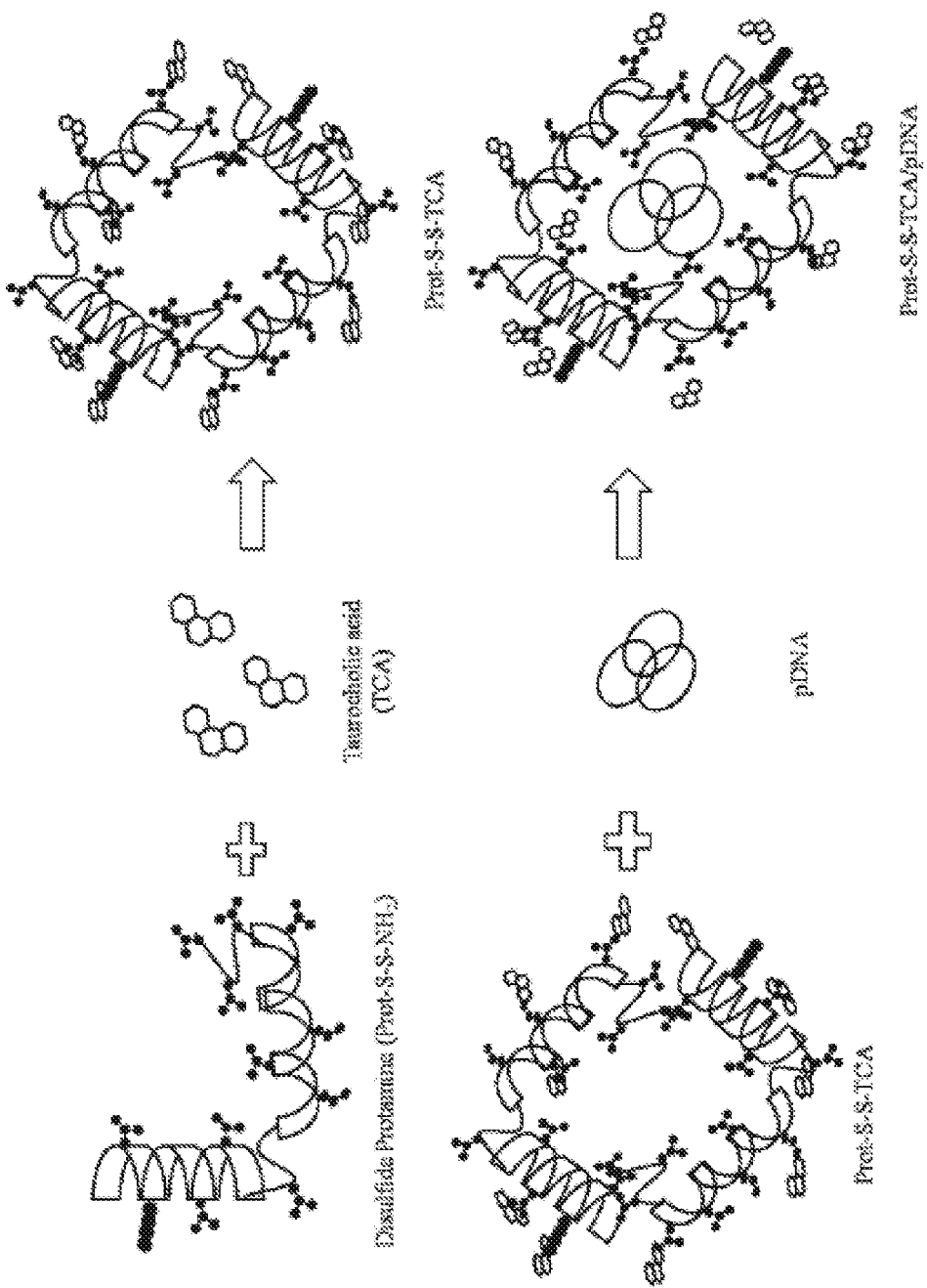

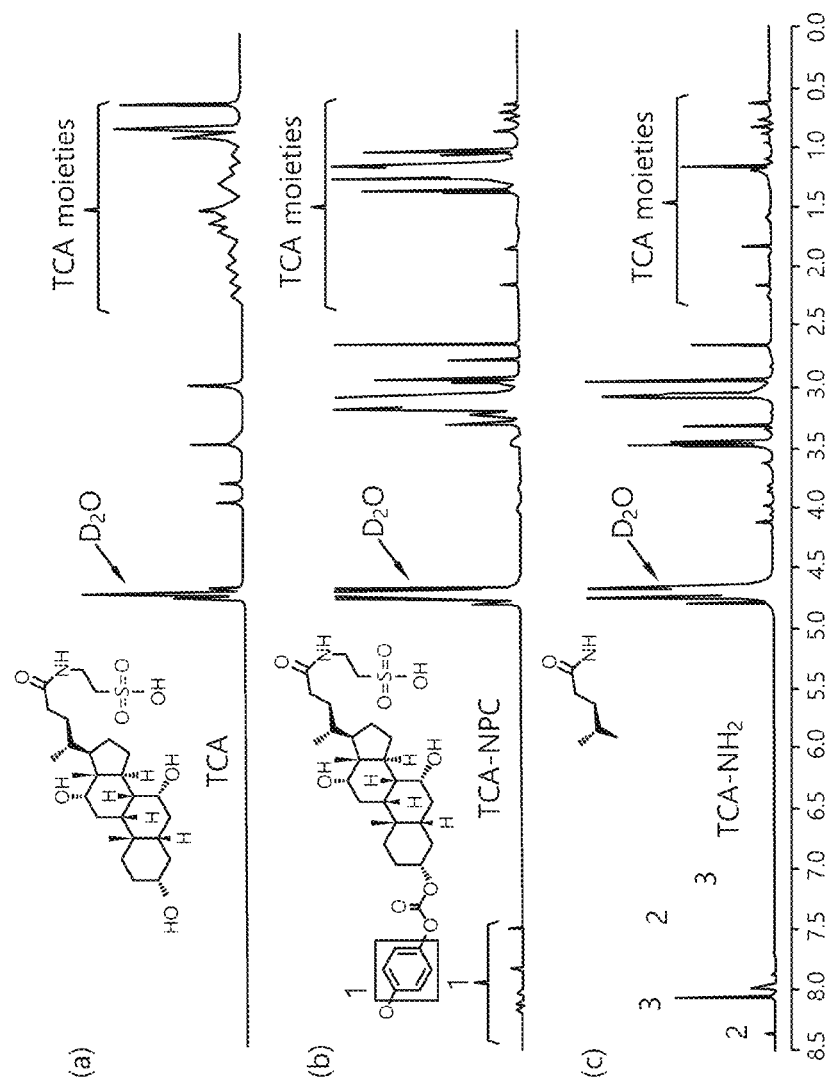
[FIG. 17]

[FIG. 18]
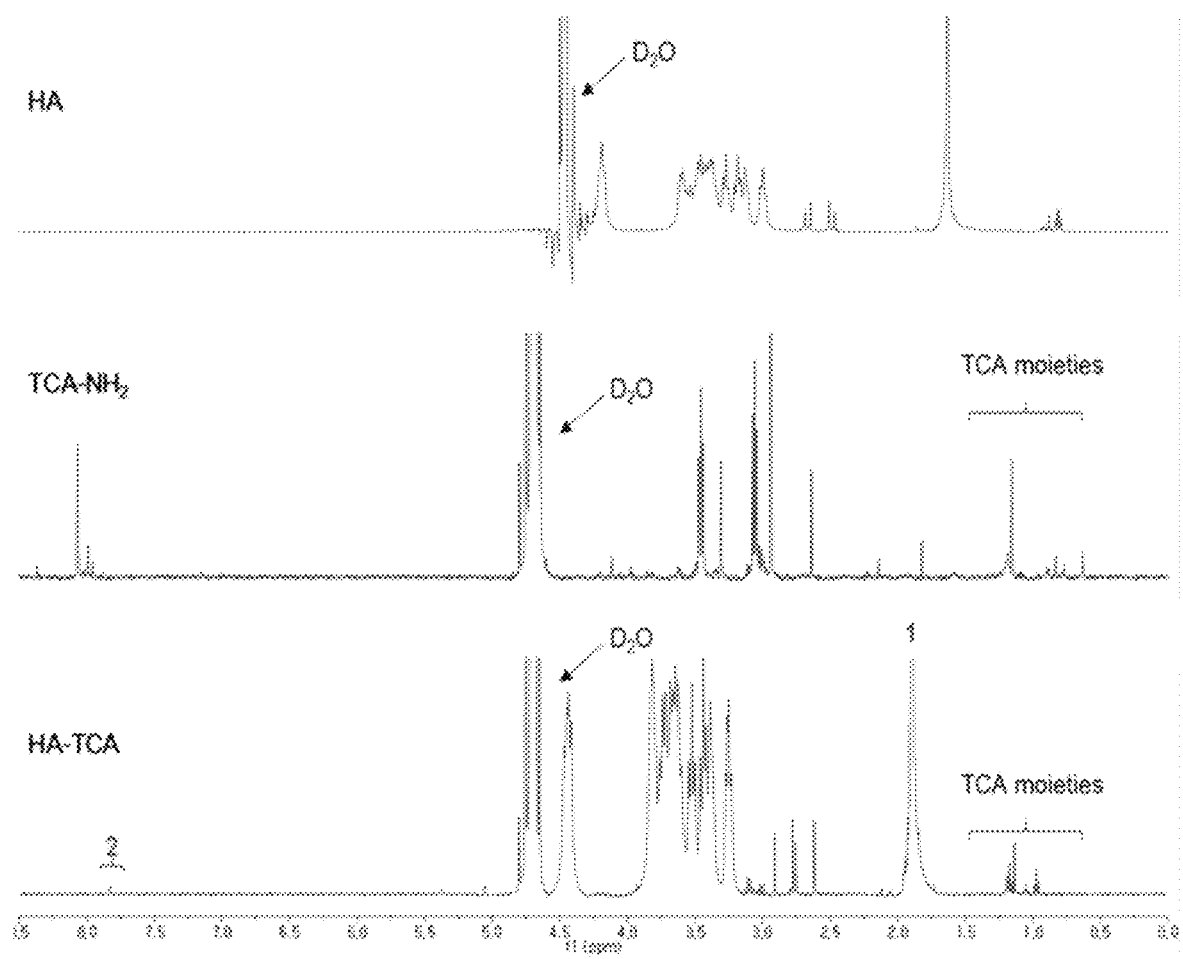

ORALLY ADMINISTERED NANOPARTICLES FOR GENE DELIVERY AND PHARMACEUTICAL COMPOSITION CONTAINING SAME

TECHNICAL FIELD

The present invention relates to a targeting nanoparticle for efficient oral gene delivery, and more particularly to a nanoparticle for gene delivery, comprising: an ionic polymer conjugated with bile acid or a bile acid derivative; and a gene, and to a pharmaceutical composition comprising the same. Moreover, the present invention relates to a nanoparticle for gene delivery, which is used to deliver a gene or a therapeutic protein to targeted small intestine cells in order to minimize side effects and provide the efficiency of current therapeutic technology, and to a pharmaceutical composition comprising the same.

BACKGROUND ART

Gene therapy treats disease by delivering a therapeutic gene to a target organ to express a new protein in cells. The gene therapy is not to treat the symptoms of disease, but is a way to treat disease by eliminating the cause of the disease. The gene therapy has better selective therapeutic effects than general drug therapies, and can be applied for a long period of time by improving the cure rate of diseases difficult to control by other therapies.

The gene therapy is a next-generation therapeutic technology disclosed for the treatment of various diseases, but when a macromolecule such as DNA, RNA or the like is delivered into cells in an aqueous solution state, it is degraded rapidly by a specific enzyme in vivo and the intracellular deliver)/rate thereof is low. For this reason, in order to make the gene therapy effective, it is essential to develop a gene carrier that can safely deliver a therapeutic gene to a target cell so as to obtain high expression efficiency.

Gene carriers should have low or no toxicity and should be able to selectively and effectively deliver genes to targeted cells. Such gene carriers may be largely divided into viral and non-viral gene carriers.

Viral vectors use retro virus (RV), adeno virus (AV), adeno-associated virus (AAV) or the like as a gene carrier, and have higher gene delivery efficiency than non-viral vectors. However, when these viral vectors are introduced into the body, the vectors themselves cause problems such as immune responses or cancer induction. In addition, there is a limitation on the size of a gene that can be inserted into the vector.

Non-viral vectors such as polymers or nanoparticles have advantages over viral vectors in that they have a low biological risk, are non-immunogenic, can be modified, and can be produced in large amounts, and the size of genes that can be delivered by them is less limited. Due to these advantages, many studies thereon have recently been conducted. In particular, methods employing non-viral vectors such as cationic polymers have been much studied because of the simplicity of production methods or a relatively low risk. In a specific mechanism, the non-viral vector stabilizes a negatively charged gene by forming a complex through electrostatic interaction with the gene, and the complex binds to the cell surface by the electrical interaction between the positive charge on the complex surface and the negative charge on the cell surface, after which the gene is released from the endosome into the cytoplasm.

Specific examples of these cationic polymers include cationic homopolymers such as protamine, polyethyleneimine (PEI), polyamidoamine, poly-L-lysine (PLL), polyaminoester, polypropyleneimine and the like, and cationic block copolymers such as polyethylene glycol (PEG)-block-poly-L-lysine and PEG-PEI. These cationic polymers protect a gene such as DNA from enzymatic degradation by compressing the gene into a nanoparticle, and help enable the gene to penetrate rapidly into cells and allow the gene to escape from the endosome.

Most non-viral vectors have advantages, such as biodegradability, low toxicity, non-immunogenicity, the ease of use, and the like, over viral vectors, but have problems such as relatively lower transfection efficiency than viral vectors, limited particle sizes, and the like.

Polyethyleneimine (PEI), which is currently most extensively studied as a non-viral vector, also has problems, such as significantly in vivo low transfection efficiency, high cytotoxicity, and low gene expression efficiency due to low blood compatibility, and the like.

Meanwhile, Korean Patent Application Publication No. 10-2010-0122405 discloses a nanoparticle-type amphiphilic polymer nanoparticle which is an siRNA carrier obtained by bonding an siRNA to an amphiphilic polymer nanoparticle, a complex comprising a hydrophilic polymer bonded to a hydrophobic polymer, and which is produced by bonding each of chitosan and polyethyleneimine as hydrophilic polymers to the bile acid 5-β-cholanic acid, thereby producing complexes, and then mixing the complexes with each other. In particular, the above patent document discloses that spherical self-aggregates are formed in an aqueous system due to amphiphilicity caused by the hydrophobic groups of bile acid and the hydrophilic group of chitosan and polyethyleneimine (PEI), and for this reason, strongly amphiphilic polyethyleneimine and chitosan are located on the surface of chitosan-bile acid/polyethyleneimine (PEI)-bile acid complex nanoparticles, and hydrophobic bile acid is located in the core. However, it is not accessible for clinical trials due to the serious toxicity of PEI.

Accordingly, there is an urgent need to develop a gene carrier for safe and efficient gene delivery, which has enhanced transfection efficiency while retaining the advantages of conventional non-viral vectors.

Meanwhile, diabetes mellitus is a metabolic disease in which the blood glucose concentration is increased due to insufficient insulin secretion or functional abnormalities. Type 2 diabetes refers to the case in which in vivo blood glucose levels are increased without being controlled, because insulin is not properly secreted or the insulin secreted does not properly act in vivo, and type 1 diabetes refers to the case in which blood glucose levels are increased because the pancreas fails to secrete insulin. In the case of type 1 diabetes, insulin treatment is necessary. In the case of type 2 diabetes, lifestyle modification is essential, and administration of oral hypoglycemic agents may additionally be required. An eating drug is administered one to three times a day, and the administration time or side effects of the drug slightly differ depending on the time of action of the drug.

Diabetes therapies which are currently used include diet therapy, exercise therapy, sulphonylureas, biguanide-based drugs, α-glucosidase inhibitors, insulin, and the like, and various insulins and the like have been developed through many studies on the development of new drugs and have been applied to clinical practice.

Meanwhile, glucagon-like peptide-1 (GLP-1), a kind of insulin secretion peptide, is an incretin hormone which is secreted from the L-cells of the ileum and large intestine. The major action of glucagon-like peptide-1 is to increase insulin secretion and to inhibit hypoglycemia by glucose-dependent insulin secretion. Due to such characteristics, glucagon-like peptide-1 is applied for the treatment of type 2 diabetes. However, it has a very short blood half-life of about 2 minutes, and for this reason, the development of drugs using glucagon-like peptide-1 is greatly limited. Accordingly, developed and commercially available glucagon-like peptide-1 agonists include exendin-4, a glucagon-like peptide-1 analogue isolated from the salivary glands of the Gila monster. Exendin-4 has higher physiological activity than glucagon-like peptide-1 together with resistance to DPP-IV (dipeptidyl peptidase-4), and thus has an in vivo half-life of 2 to 4 hours, which is longer than that of glucagon-like peptide-1 (U.S. Pat. No. 5,424,286). However, it is impossible to expect the sufficient duration of physiological activity only by a method that increases resistance to DPP-IV. For example, currently commercially available exendin-4 (exenatide) should be administered twice a day to a patient through injection, and still has a disadvantage in that vomiting and nausea due to administration of exenatide impose a great burden on patients.

However, these therapeutic agents have low efficacy or the problem of causing many side effects such as liver dysfunction, hypoglycemia, lactic acidosis and the like.

Accordingly, there is a need for a diabetes therapeutic agent that reduces the adverse effects of conventional diabetes therapeutic agents, improves metabolic abnormalities, and is safe even when administered over a long period of time.

In addition, in order to solve these problems, a technology employing viral carriers has been developed. This technology is exposed to risks such as nonspecific immune responses, etc., and the production process is complicated, resulting in many problems in commercialization. Therefore, recent studies have been directed toward the use of non-viral carriers, that is, carriers based on cationic lipids or polymers. Although the efficiency of these non-viral carriers is lower than that of viral carriers, these non-viral carriers have advantages in that they are stable in vivo, are produced by an easy and simple process, and are low-priced. However, when a mixture is to be made using a polymer and a gene, formation of the mixture encounters great difficulty due to the characteristic hardness and weakly anionic nature of the gene.

DISCLOSURE

Technical Problem

Accordingly, the present inventors have conducted studies and made efforts to solve the above-described problems, and as a result, have found that when a nanoparticle for gene deliver)/comprises an ionic polymer, surface-modified with bile acid or a bile acid derivative, and a gene, and when the core of the nanoparticle for gene deliver)/comprises an ionic complex of the ionic polymer and the gene and when the bile acid or bile acid derivative having an hydrophilic ionic group is located on the surface of the nanoparticle, the in vivo stability of the nanoparticle can be improved, the above-described side effects can be reduced by minimizing the in vivo toxicity of the nanoparticle, and disorders associated with oral administration of the nanoparticle can be overcome, thereby completing the present invention.

Therefore, it is an object of the present invention to provide a nanoparticle for gene delivery, which is capable of effectively delivering a therapeutic gene to an intracellular target site and comprises: at least one ionic polymer conjugated with bile acid or a bile acid derivative; and a gene, wherein the conjugated bile acid or bile acid derivative has an ionic group.

Another object of the present invention is to provide a pharmaceutical composition for treating diabetes, which comprises the nanoparticle for gene delivery as an active ingredient.

Technical Solution

To achieve the above objects, the present invention provides a nanoparticle for gene delivery, which comprises: at least one ionic polymer conjugated with bile acid or a bile acid derivative; and a gene, wherein the conjugated bile acid or bile acid derivative has an ionic group.

In one embodiment of the present invention, the ionic polymer may be a cationic polymer.

In one embodiment of the present invention, the cationic polymer may be selected from the group consisting of chitosan, protamine, poly-L-lysine (PLL), and polyamidoamine (PAMAM).

In one embodiment of the present invention, the ionic polymer may be an anionic polymer, and in this case, the ionic polymer further comprises a cationic polymer.

In one embodiment of the present invention, the anionic polymer may be selected from among heparin, hyaluronic acid, and chondroitin sulfate, and the cationic polymer may be selected from the group consisting of chitosan, glycol chitosan, protamine, poly-L-lysine (PLL), and polyamidoamine (PAMAM).

In one embodiment of the present invention, the ionic polymer conjugated with the bile acid or bile acid derivative may be one conjugated via a disulfide bond.

In one embodiment of the present invention, the bile acid or its derivative may be selected from the group consisting of deoxycholic acid, taurodeoxycholic acid, taurocholic acid (TCA), glycocholic acid, and glycochenodeoxycholic acid. More preferably, it is taurocholic acid (TCA).

In one embodiment of the present invention, the gene may be one or more selected from among single-stranded or double-stranded DNA (deoxyribonucleic acid), single-stranded or double-stranded RNA (ribonucleic acid), plasmid DNA (pDNA), antisense oligonucleotides, ribozymes, catalytic RNA, and nucleotides. Preferably, the gene may be one or more selected from among plasmid DNA (pDNA) and antisense oligonucleotides. More preferably, the gene may be a glucagon-like peptide-1 (GLP-1) gene, a GLP-1 peptide, a GLP-1 variant, a GLP-1 derivative, a GLP-1 agonist, liraglutide, or exendin-4.

In one embodiment of the present invention, the degree of conjugation of the bile acid or its derivative may vary depending on the number of functional groups of the ionic polymer, but the bile acid or its derivative and the ionic polymer may preferably be conjugated to each other at a molar ratio of 1:1 to 1:300.

In one embodiment of the present invention, the nanoparticle for gene delivery may be absorbed regardless of the particle size, but may preferably have a particle size of 500 nm or less.

In one embodiment of the present invention, the ionic polymer conjugated with the bile acid or bile acid derivative and the gene may be bonded to each other at a molar ratio of 1:1 to 1:200.

In one embodiment of the present invention, the N/P ratio (the number of nitrogen atoms of the ionic polymer conjugated with the bile acid or bile acid derivative/the number of phosphate atoms of the gene) of the nanoparticle for gene delivery may be 1 to 200.

The present invention also provides a pharmaceutical composition for treating diabetes, which comprises a nanoparticle for gene delivery as an active ingredient, wherein the nanoparticle comprises: at least one ionic polymer conjugated with bile acid or a bile acid derivative; and a glucagon-like peptide-1 (GLP-1) gene, a GLP-1 peptide, a GLP-1 variant, a GLP-1 derivative, a GLP-1 agonist, liraglutide, or exendin-4, wherein the conjugated bile acid or bile acid derivative has an ionic group.

In one embodiment of the present invention, the composition may be for oral administration.

Advantageous Effects

The nanoparticle for gene delivery according to the present invention is a novel oral gene delivery system capable of regulating blood glucose levels in biological systems and insulin secretion in response to ingested meals, and comprises: an ionic polymer conjugated with bile acid or a bile acid derivative; and a gene.

The nanoparticle for gene delivery according to the present invention is a nanoparticle surface-modified with bile acid or its derivative, wherein an ionic complex comprising a negatively charged gene encapsulated in a cationic polymer due to the electrostatic interaction between the negatively charged gene and the cationic polymer is present in the core of the nanoparticle and wherein the bile acid or bile acid derivative conjugated to the cationic polymer is located on the surface of the nanoparticle while having a hydrophilic anionic group.

Furthermore, the nanoparticle for gene delivery according to the present invention is a nanoparticle surface-modified with bile acid or its derivative, wherein an ionic complex comprising a negatively charged gene encapsulated in a cationic polymer due to the electrostatic interaction between the negatively charged gene and the cationic polymer is present in the core of the nanoparticle and wherein the cationic polymer of the ionic complex, and the anionic polymer conjugated with the bile acid or bile acid derivative having a hydrophilic anionic group, are conjugated to each other by electrostatic interaction, and thus the bile acid or bile acid derivative conjugated to the anionic polymer is located on the surface of the nanoparticle while having a hydrophilic ionic group.

Accordingly, the nanoparticle for gene delivery according to the present invention protects against gastric acid through direct physical bonding between the cationic polymer and the gene, may be safely delivered to small intestine cells, and may also be used as a targeting nanoparticle that enables the GLP-1 gene to be expressed only in L-cells in the small intestine.

When the nanoparticle surface-modified with bile acid or its derivative according to the present invention was used to deliver a therapeutic gene to a target cell, it easily delivered the gene through intestinal mucosa and, at the same time, was very stable in the gastrointestinal tract due to the ionic complex present in the core of the nanoparticle. This suggests that the nanoparticle for gene delivery according to the present invention is very suitable for oral administration.

The bile acid located on the surface of the nanoparticle according to the present invention can inhibit gastrointestinal (GI) degradation of the nanoparticle, and absorb the bile acid receptor ASBT (apical sodium bile acid transporter) receptor of intestinal cell membrane in the small intestine ileum, thereby delivering the therapeutic gene into cells, and thus the nanoparticle can exhibit increased gene expression.

In particular, when the therapeutic gene used is GLP-1, a GLP-1 peptide, a GLP-1 variant, a GLP-1 derivative, a GLP-1 agonist, liraglutide or exendin-4, the bile acid located on the surface of the nanoparticle according to the present invention and the cationic polymer are separated by the enzyme glutathione of intestinal cells and pH and enter portal vein, and the separated therapeutic gene is delivered only to the nucleus of intestinal cells and expresses a large amount of the GLP-1, GLP-1 peptide, GLP-1 variant, GLP-1 derivative, GLP-1 agonist, liraglutide or exendin-4, thereby efficiently exhibiting diabetic therapeutic efficacy.

Accordingly, the nanoparticle for gene delivery according to the present invention, when administered orally to diabetic mouse models, can exhibit blood glucose-lowering effects by secreting insulin while successfully expressing GLP-1, a GLP-1 peptide, a GLP-1 variant, a GLP-1 derivative, a GLP-1 agonist, liraglutide or exendin-4, thereby effectively preventing or treating diabetes, particularly type 2 diabetes.

DESCRIPTION OF DRAWINGS

FIG. 1 is a schematic diagram showing a process in which a nanoparticle for gene delivery according to the present invention is absorbed through ileal ASBT.

FIG. 2 is a reaction scheme showing a process for producing Prot-TCA in Example 1.

FIG. 3 shows the $^1$H NMR of Prot-TCA produced in Example 1.

FIG. 4 is a reaction scheme showing a process for producing CS-TCA in Example 2.

FIG. 5 shows the $^1$H NMR of CS-TCA produced in Example 2.

FIG. 6 is a reaction scheme showing a process for producing PAMAM-TCA in Example 3.

FIG. 7 is a reaction scheme showing a process for producing PLL-TCA in Example 4.

FIG. 8 is a reaction scheme showing a process for producing pDNA/Prot-TCA in Example 7.

FIG. 9 is a reaction scheme showing a process for producing Hep-S—S—NH2 in Example 11.

FIG. 10 is a reaction scheme showing a process for producing TCA-NPC in Example 11.

FIG. 11 is a reaction scheme showing a process for producing Hep-S—S-TCA in Example 11.

FIG. 12 shows the $^1$H NMR of the Hep-S—S—NH2 and Hep-S—S-TCA produced in Example 11.

FIG. 13 is a reaction scheme showing a process for producing CS—S—S-TCA in Example 13.

FIG. 14 shows the $^1$H NMR of CS—S—S-TCA produced in Example 13.

FIG. 15 is a reaction scheme showing a process for producing Prot-S—S-TCA in Example 15.

FIG. 16 is a reaction scheme showing a process for producing pDNA/Prot-S—S-TCA in Example 16.

FIG. 17 shows the $^1$H NMR of the TCA-NPC and TCA-NH2 produced in Example 17.

FIG. 18 shows the $^1$H NMR of HA-TCA produced in Example 17.

MODE FOR INVENTION

Hereinafter, the present invention will be described in more detail. Unless otherwise defined, the scientific and technical terms used herein have the same meanings as commonly understood by those skilled in the technical field to which the present invention pertains. In the following description, the detailed description of known functions and configurations will be omitted when it may unnecessarily obscure the subject matter of the present invention.

Hereinafter, the present invention will be described in more detail.

The present invention provides a nanoparticle for gene delivery, which a novel oral gene delivery system and comprises: at least one ionic polymer conjugated with bile acid or a bile acid derivative; and a gene, wherein the conjugated bile acid or bile acid derivative has an ionic group.

The gene is in the form of a negatively charged large polymer chain. When the gene is present alone, it has a random coil shape having a relatively large volume, and thus it is difficult to deliver the gene into cells. For this reason, a cationic polymer is used which can form a nano-sized ionic complex with the gene through electrostatic interaction.

The nanoparticle for gene delivery according to the present invention comprises an ionic complex of a gene with an ionic polymer. The ionic polymer forming the ionic complex with the anionic gene should essentially be a cationic polymer, wherein the cationic polymer may be one conjugated with bile acid.

The nanoparticle for gene delivery according to the present invention may be formed by electrostatic interaction between the gene and the cationic polymer conjugated with bile acid or its derivative, or may be formed by electrostatic interaction between an anionic polymer conjugated with bile acid or its derivative, the cationic polymer and the gene, and may more safely induce cell internalization of the gene.

Namely, the nanoparticle for gene delivery according to the present invention is a nanoparticle surface-modified with bile acid, wherein the ionic complex of the cationic polymer with the gene is present in the core of the nanoparticle and the bile acid having a hydrophilic ionic group is located on the surface of the nanoparticle.

When the nanoparticle surface-modified with bile acid or its derivative according to the present invention was used to deliver a therapeutic gene to a target cell, it easily delivered the gene through intestinal mucosa and, at the same time, was very stable in the gastrointestinal tract due to the ionic complex present in the core of the nanoparticle. This suggests that the nanoparticle for gene delivery according to the present invention is very suitable for oral administration.

In one embodiment of the present invention, the ionic polymer may be a cationic polymer. When the ionic polymer is a cationic polymer, the negatively charged gene is encapsulated in the cationic polymer due to electrostatic interaction with the cationic polymer, thereby forming an ionic complex. The formed ionic complex is located in the core of the nanoparticle, and the bile acid or bile acid derivative conjugated to the cationic polymer is located on the surface of the nanoparticle while having a hydrophilic ionic group.

In one embodiment of the present invention, the cationic polymer may be a nontoxic polymer having a weight-average molecular weight of 100 to 100,000. For example, it may be selected from the group consisting of chitosan (CS), glycol chitosan, protamine (Prot), poly-L-lysine (PLL), and polyamidoamine (PAMAM). Preferably, it may be chitosan (CS), protamine (Prot), poly-L-lysine (PLL), or polyamidoamine (PAMAM).

Chitosan is a naturally occurring, very safe cationic polysaccharide having a structure of (1->4) 2-amino-2-deoxy-β-D-glucan. Chitosan is a basic polysaccharide produced by N-deacetylation of chitin obtained from natural crustaceans or the like, and is known to show biodegradability, biocompatibility and low cytotoxicity. In the present invention, it is preferable to use either water-soluble chitosan, which is a natural polymer having excellent biodegradability and biocompatibility, or glycol chitosan having increased water solubility due to a glycol group introduced therein.

Protamine is a natural cationic protein rich in arginine, and is abundantly present in animal testicles, particularly the sperm nucleus of fishes, including salmon, and is known to be involved in genetic information expression through association with or dissociation from DNA, like histone. Generally, the molecular weight of protamine extracted from the sperm nucleus of fish is about 4,000 to 10,000, and 70% or more of the constituent amino acids of protamine are arginines, but the scope of the present invention is not limited thereto. Protamine of the present invention includes all protamine itself and a pharmaceutically acceptable salt thereof. Specifically, a salt of protamine of the present invention includes a salt formed with acidic substance, including hydrochloride or sulfate. Protamine may be used in any form, because it is soluble in water without salt formation and a salt thereof is also soluble in water.

Poly-L-lysine (PLL) is linked by a biodegradable peptide bond, and thus can form an ionic complex with a gene and can be delivered to cells. However, it is somewhat toxic, and thus when it is used alone, it is difficult to show high delivery efficiency. For this reason, it may be used in a state in which an endosome-disruptive substance, an endosome fusion peptide or the like is attached thereto.

In one embodiment of the present invention, the ionic polymer may be an anionic polymer, and in this case, it essentially further comprises a cationic polymer in order to form an ionic complex with the gene. Namely, the negatively charged gene is encapsulated in the cationic polymer due to electrostatic interaction with the cationic polymer, thereby forming an ionic complex, and the formed ionic complex is located in the core of the nanoparticle. The anionic polymer is bonded to the cationic polymer of the ionic complex by electrostatic interaction, and the bile acid or bile acid derivative conjugated to the anionic polymer is located on the surface of the nanoparticle while having a hydrophilic ionic group.

In one embodiment of the present invention, the anionic polymer may be selected from among heparin, hyaluronic acid, and chondroitin sulfate, and the cationic polymer may be selected from the group consisting of chitosan, glycol chitosan, protamine, poly-L-lysine (PLL), and polyamidoamine (PAMAM).

Heparin has a structure comprising a hydroxyl group, a carboxyl group and an amino group, and heparin which is used may be non-fractionated heparin, high-molecular-weight heparin, low-molecular-weight heparin, a heparin fragment, recombinant heparin, a heparin analogue, heparan sulfate, a sulfonated polysaccharide having heparin activity, or the like.

In one embodiment of the present invention, the bile acid or its derivative has a hydrophilic anionic group in addition to a functional group capable of conjugating to the ionic polymer, and may be selected from the group consisting of deoxycholic acid (DCA), taurodeoxycholic acid, taurocholic acid (TCA), glycocholic acid, and glycochenodeoxycholic acid. More preferably, it taurocholic acid (TCA) having four or more hydrophilic anionic groups.

The bile acid is absorbed into the liver through the ileum of small intestine with a high efficiency of 95% or more, and this absorption is referred to as 'enterohepatic circulation'.

The bile acid is a biological surfactant playing an important role in lipid migration by this enterohepatic circulation, and may act as a targeting ligand in oral delivery because it is recognized specifically by ASBT (apical sodium-dependent bile acid transporter) present in a distal intestinal portion.

Namely, the bile acid which is absorbed through the ileum is located on the surface of the nanoparticle for gene delivery, and thus functions to increase the uptake of the nanoparticle for gene delivery into target cells through the intestinal inner wall, which is the biggest problem of a conventional oral administration method performed through ASBT (FIG. 1). For this reason, the nanoparticle for gene delivery according to the present invention can be easily absorbed through the ileum that absorbs the bile acid, and thus it may be used for oral administration, thereby increasing the bioavailability of the drug.

In one embodiment of the present invention, the ionic polymer conjugated with the bile acid or bile acid derivative may be one conjugated via a disulfide bond.

A disulfide bond (S—S) has a tendency to respond sensitively to and be separated easily from glutathione which is abundantly secreted from intestinal cells. Thus, when the nanoparticle for gene delivery according to the present invention approaches intestinal cells, it is mostly separated and only the gene enters the nucleus of L-cells. The entered gene is expressed and functions to restore damaged function by expressing the GLP-1 peptide. In addition, the disulfide bond also plays a role in minimizing non-specific delivery to other organs or cells.

In one embodiment of the present invention, the kind of gene that may be bonded to the nanoparticle for gene delivery according to the present invention is not particularly limited, and any gene, which may be delivered to a desired target according to the purpose of the present invention and may exhibit a desired therapeutic effect, falls within the scope of the present invention. For example, the gene of the present invention may include a normal gene for a disease-related therapeutic gene, a gene for inhibiting expression of a target protein, a large or small polynucleotide including an antisense polynucleotide, ribozyme, or any RNA-type gene including siRNA. Specifically, the gene may be one or more selected from among single-stranded or double-stranded DNA (deoxyribonucleic acid), single-stranded or double-stranded RNA (ribonucleic acid), plasmid DNA (pDNA), antisense oligonucleotides, ribozyme, catalytic RNA, and nucleotides. Preferably, the gene may be one or more selected from among plasmid DNA (pDNA) and antisense oligonucleotides. The gene may be a gene drug, and as used herein, the gene drug refers to a drug that exhibits a medicinal effect on the prevention or treatment of one or more diseases.

The gene may be a gene encoding GLP-1 which is an insulin secretion peptide. Preferably, the gene may be glucagon like peptide-1 (GLP-1) gene, a GLP-1 peptide, a GLP-1 variant, a GLP-1 derivative, a GLP-1 agonist, liraglutide, or exendin-4.

In the present invention, the terms "GLP-1 gene" and "GLP-1 variant" are used to denote the nucleic acid (DNA) molecules encoding the respective genes. In addition, the terms "GLP-1 agonist", "liraglutide" or "exendin-4", etc., when refer to a list of genes, are used to denote nucleic acid (DNA) molecules encoding the respective peptides or proteins.

The GLP-1 gene, GLP-1 variant or GLP-1 derivative may all be included in a circular or linear plasmid for expression. The GLP-1 variant may be, for example, GLP-1 (7-34), GLP-1 (7-35), GLP-1 (7-36), Val$^8$-GLP-1 (7-37), Gln$^8$-GLP-1 (7-37), D-Gln$^9$-GLP-1 (7-37), Thr$^{18}$-Lys$^{18}$-GLP-1 (7-37), Lys$^{18}$-GLP-1 (7-37), His$^7$-GLP-1 (7-37), Ser$^8$-GLP-1 (7-37) or Tyr$^8$-GLP-1 (7-37), the sequence of which is disclosed in US 2013-0210717 A1. When the nanoparticle for gene delivery, prepared by forming a complex with the above-described GLP-1 gene, GLP-1 peptide, GLP-1 variant, GLP-1 derivative, GLP-1 agonist, liraglutide or exendin-4, is administered in vivo, it can exhibit excellent blood glucose lowering effects, thereby effectively preventing or treating diabetes, particularly type 2 diabetes.

In one embodiment of the present invention, the degree of conjugation of the bile acid or its derivative may vary depending on the number of functional groups of the ionic polymer. Preferably, the bile acid or its derivative and the ionic polymer may be conjugated to each other at a molar ratio of 1:1 to 1:300.

Preferably, the bile acid or its derivative and a cationic polymer may be conjugated to each other at a molar ratio of 1:1 to 1:100.

Preferably, the bile acid or its derivative and heparin may be conjugated to each other at a molar ratio of 1:1 to 1:30.

Preferably, the bile acid or its derivative and hyaluronic acid may be conjugated to each other at a molar ratio of 1:1 to 1:200.

In one embodiment of the present invention, although the nanoparticle for gene delivery may be absorbed regardless of the particle size, it may preferably have a particle size of 500 nm or less, more preferably 100 to 300 nm.

In one embodiment of the present invention, the zeta potential of the nanoparticle for gene delivery may vary depending on the kind of ionic polymer used on the surface of the nanoparticle. Specifically, a nanoparticle for gene delivery, formed by electrostatic interaction between a gene and a cationic polymer conjugated with bile acid or its derivative, may show a zeta potential ranging from 10 to 30 mV. In addition, a nanoparticle for gene delivery, formed by electrostatic interaction between a gene, a cationic polymer and an anionic polymer conjugated with bile acid or its derivative, may show a zeta potential ranging from −10 to −30 mV.

In one embodiment of the present invention, the ionic polymer conjugated with the bile acid or bile acid derivative and the gene may be bonded to each other at a molar ratio of 1:1 to 1:200, preferably 1:1 to 1:100. In the bonding ratio range, the expression level of the gene is not adversely affected, and cell growth is not adversely affected by the cytotoxicity of the nanoparticle for gene delivery which is delivered into the cells.

In one embodiment of the present invention, the cationic polymer conjugated with the bile acid or bile acid derivative and the gene may be mixed with each other at a weight ratio/molar ratio of 1:1 to 1:200, preferably 1:3 to 1:30. Since there is a limit to the bonding ability of the cationic polymer and delivery is possible only in the range in which the cationic polymer can have optimal strong bonding ability, the ionic complex is easily formed by electrostatic interaction between the cationic polymer and the gene in the above-described ratio range.

In one embodiment of the present invention, the anionic polymer conjugated with the bile acid or bile acid derivative, the cationic polymer and the gene may be mixed with one another by a weight ratio/molar ratio of 3:1:1 to 10:1:200, preferably 3:1:1 to 10:1:30. This ratio range is an optimal range in which the bonding ability can be maintained by charge-to-charge interactions. Outside this range, the formulation is not made and the stability is lost.

In one embodiment of the present invention, the N/P ratio (the number of nitrogen atoms of the ionic polymer (particularly the cationic polymer) conjugated with the bile acid or bile acid derivative/the number of phosphate atoms of the gene) of the nanoparticle for gene delivery is 1 to 200. When the N/P ratio is in this range, the stabilization of the gene by the cationic polymer can be facilitated, and thus the uptake of the gene into cells can be increased and a stable nanoparticle for gene delivery can be formed.

The present invention also provides a pharmaceutical composition for treating diabetes, which comprises a nanoparticle for gene delivery as an active ingredient, wherein the nanoparticle comprises: at least one ionic polymer conjugated with bile acid or a bile acid derivative; and a glucagon-like peptide-1 (GLP-1) gene, a GLP-1 peptide, a GLP-1 variant, a GLP-1 derivative, a GLP-1 agonist, liraglutide, or exendin-4, wherein the conjugated bile acid or bile acid derivative has an ionic group.

The nanoparticle for gene delivery comprises, as a therapeutic gene, a glucagon-like peptide-1 (GLP-1) gene, a GLP-1 peptide, a GLP-1 variant, a GLP-1 derivative, a GLP-1 agonist, liraglutide or exendin-4, which is a kind of insulation secretion peptide. Thus, it increases insulin secretion by being uptaken into target cells, and induces glucose-dependent insulin secretion, thereby preventing the occurrence of hypoglycemia. Accordingly, it may be advantageously used for treatment of diabetes, particularly type 2 diabetes.

The term "active ingredient" in the present invention includes having an activity of preventing or treating diabetes when the composition is administered to a subject, compared to otherwise. The subject may be at least one selected from the group consisting of mammals, for example, humans, mice, hamsters, dogs, cats, horses, cattle, pigs and goats. The term "preventing" includes preventing the blood glucose concentration from increasing, compared to when the composition is not administered. The term "treating" includes lowering the blood glucose concentration compared to when the composition is not administered.

In addition, the pharmaceutical composition of the present invention may comprise the nanoparticle for gene delivery alone or may further comprise one or more pharmaceutically acceptable carriers, adjuvants or excipients.

In addition, the pharmaceutical composition of the present invention may be prepared into conventional formulations known in the pharmaceutical field, for example, oral dosage formulations such as tablets, pills, soft/hard capsules, liquids, suspensions, emulsions, syrups, granules, elixirs or the like, or parenteral dosage formulations such as sterilized aqueous or oil-based solutions for intravenous, subcutaneous, sublingual or intramuscular administration.

Pharmaceutically acceptable carriers that may be used in the pharmaceutical composition of the present invention are those that are generally used in formulation, and include, but are not limited to, lactose, dextrose, sucrose, sorbitol, mannitol, starch, Arabia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and/or mineral oil, etc.

Excipients that may be used in the pharmaceutical composition of the present invention include sweeteners, binders, dissolving agents, dissolution aids, wetting agents, emulsifying agents, isotonizing agents, adsorbents, disintegrants, antioxidants, preservatives, lubricants, fillers, fragrances, and the like. The proportion and nature of such excipients may be determined by the solubility and chemical properties of the tablet selected, the chosen route of administration, and standard pharmaceutical practice. Examples of excipients include lactose, dextrose, sucrose, mannitol, sorbitol, cellulose, glycine, silica, talc, stearic acid, stearin, magnesium stearate, magnesium aluminosilicate, starch, gelatin, tragacanth rubber, alginic acid, sodium alginate, methyl cellulose, sodium carboxymethyl cellulose, agar, water, ethanol, polyethylene glycol, polyvinylpyrrolidone, sodium chloride, calcium chloride, orange essence, strawberry essence, vanilla fragrance, and the like.

In addition, the pharmaceutical composition of the present invention may also be formulated as a parenteral dosage form. In this case, intravenous administration, intraperitoneal administration, intramuscular administration, subcutaneous administration, local administration or the like may be used, but is not limited thereto. To provide the formulation for parenteral administration, the pharmaceutical composition may be prepared into a solution or suspension by mixing the active ingredient (i.e., the nanoparticle for gene delivery) with a stabilizer or a buffer in water, and this solution or suspension may be prepared as a unit dosage form of ampules or vials.

More preferably, the pharmaceutical composition according to the present invention may be an oral dosage formulation.

In addition, the pharmaceutical composition of the present invention may be sterilized or may further comprise pharmaceutical excipients, such as a preservative, stabilizing agent, hydrating agent or emulsification accelerator, salt for adjusting osmotic pressure, and/or buffer. Furthermore, it may further comprise other therapeutically useful substances, and may be formulated according to a conventional method, such as mixing, granulation or coating.

The dose of administration of the nanoparticle for gene delivery, which is the active ingredient of the pharmaceutical composition according to the present invention, to mammals including human beings, may vary depending on the patient's age, weight, sex, the mode of administration, health conditions and the severity of the disease. The pharmaceutical composition may be administered once or twice or more per day via an oral or parenteral route.

Hereinafter, the present invention will be described in more detail with reference to specific examples. The following examples are to illustrate the present invention, and the scope of the present invention is not limited by these examples. Unless otherwise defined, the scientific and technical terms used herein have the same meanings as commonly understood by those skilled in the technical field to which the present invention pertains. In addition, the repeated description of the same technical configurations and actions as those in the prior art will be omitted.

Materials:

Low-molecular-weight heparin (Hep, average MW: 5000 Da) was purchased from Mediplex Co., Ltd. (Korea), and sodium hyaluronate (MW: 83 kDa) was purchased from Bioland Co., Ltd. (Korea). TCA (PluronicTaurocholic acid sodium salt), DMF (dimethyl formamide), protamine (Prot), chitosan (CS), acetone, 4-NPC (4-methyl morpholin, 4-nitrophenyl chloroformate), TEA (trimethylamine), NHS (N-hydroxysuccinimide), EDC (N-(3-dimethylaminopropyl)-N'-ethylcarbodiimide hydrochloride), EDA (ethylene diamine) and cystamine dichloride were purchased from Sigma Chemical Co. (St. Louis, Mo.). Caco-2 cells, MDCK-ASBT and MDCK cell lines were purchased from the Korean Cell Line Bank. As pDNA gene, plasmid DNA (Sigma-Aldrich, Product Codes D4154 and D3404) derived from *Escherichia coli* RR1 was used.

Production of Cationic Polymers Conjugated with Bile Acids

Example 1: Production of Protamine-Taurocholic Acid Conjugate (Hereinafter Referred to as 'Prot-TCA')

TCA (taurocholic acid) (1 mmol) was dissolved in DMSO (dimethyl sulfoxide) (5 mL) at 0° C. until a transparent solution was formed. Then, TEA (triethylamine) (3 mmol) and 4-NPC (4-nitrophenyl chloroformate) (2.5 mmol) were sequentially added, followed by reaction at 0° C. for 30 min and at room temperature for 30 min. Prot (Protamine) (0.1 mmol) was dissolved in double-distilled water (10 mL), and then added to the reaction solution, followed by reaction at room temperature for 24 hours. The reaction solution was dialyzed with double-distilled water through a dialysis membrane (MWCO: 1000 Da) for 3 days while the medium was replaced every 6 hours. After dialysis, the reaction product was freeze-dried to yield Prot-TCA (yield: 78±2%; FIG. 2).

$^1$H NMR and TNBSA analysis indicated that taurocholic acid was conjugated to protamine (FIG. 3).

Example 2: Production of Chitosan-Taurocholic Acid Conjugate (Hereinafter Referred to as 'CS-TCA')

TCA (1 mmol) was dissolved in DMSO (5 mL) at 0° C. until a transparent solution was formed. Then, TEA (3 mmol) and 4-NPC (2.5 mmol) were sequentially added, followed by reaction at 0° C. for 30 min and at room temperature for 30 min. CS (chitosan) (0.01 mmol) was dissolved in double-distilled water (20 mL), and then added to the reaction solution, followed by reaction at room temperature for 24 hours. The reaction solution was dialyzed with double-distilled water through a dialysis membrane (MWCO: 1000 Da) for 3 days while the medium was replaced every 6 hours. After dialysis, the reaction product was freeze-dried to yield CS-TCA (yield: 92±2%; FIG. 4).

$^1$H NMR and TNBSA analysis indicated that taurocholic acid was conjugated to chitosan (FIG. 5).

(Structural Analysis)

The Prot-TCA and CS-TCA were produced by conjugating the amino group of each of Prot and CS to the hydroxyl group of TCA. To confirm it, each of Prot-TCA and CS-TCA was dissolved in D20 at 10 mg/mL, and then subjected to $^1$H NMR analysis. The results are shown in FIGS. 3 and 5, and as can be seen therein, the peaks of amide bond conjugation between TCA and Prot and amide bond conjugation between TCA and CS were detected at δ 8 ppm.

In addition, in order to examine the amino group contents of Prot-TCA and CS-TCA, the degree of amination after conjugation of TCA to each of Prot and CS was quantified by TNBSA (trinitro benzene sulphonate) analysis. As a result, it was confirmed that the amino group content of Prot-TCA was 53% compared to before TCA conjugation to Prot, indicating that the amino group content was reduced after conjugation of TCA.

Example 3: Production of Polyamidoamine-Taurocholic Acid Conjugate (Hereinafter Referred to as 'PAMAM-TCA')

PAMAM-TCA was produced in the same manner as described in Example 1, except that polyamidoamine was used instead of Prot (protamine). The structure of PAMAM-TCA was analyzed by FT-IR and FT-NMR (yield: 50%; FIG. 6).

Example 4: Production of Poly-L-Lysine-Taurocholic Acid Conjugate (Hereinafter Referred to as 'PLL-TCA')

PLL-TCA was produced in the same manner as described in Example 1, except that poly-L-lysine was used instead of Prot (protamine). The structure of PLL-TCA was analyzed by FT-IR and FT-NMR (yield: 55%; FIG. 7).

Production of Nanoparticles Comprising Bile Acid-Conjugated Cationic Polymer and Gene

Example 5: Production of Nanoparticle Comprising Protamine-Taurocholic Acid Conjugate and GLP-1-Encoding Gene (Hereinafter Referred to as 'Prot-TCA/GLP-1')

Prot-TCA (1 mg/mL) dissolved in 10 mM HEPES buffer (pH 7.4) was used as a stock solution. GLP-1 (glucagon like peptide-1)-encoding gene (7.780 mg) was dissolved in 10 mM HEPES buffer (pH 7.4) (1.922 mL), thereby preparing a GLP-1 gene solution. Under gentle vortexing, the GLP-1 gene solution (10 mL) was added dropwise to the stock Prot-TCA solution (10 mL). Thereafter, the reaction product was left to stand at room temperature for 1 hour and freeze-dried for 2 days to obtain Prot-TCA/GLP-1 (FIG. 8).

Example 6: Production of Nanoparticle Comprising Chitosan-Taurocholic Acid Conjugate and GLP-1-Encoding Gene (Hereinafter Referred to as 'CS-TCA/GLP-1')

CS-TCA/GLP-1 was obtained in the same manner as described in Example 5, except that CS-TCA was used instead of Prot-TCA of Example 5.

In order to analyze particle size and zeta potential, each of Prot-TCA/GLP-1 (Example 5) and CS-TCA/GLP-1 (Example 6) was dissolved in D20 at 1 mg/mL.

(Morphological Analysis of Nanoparticles)

Using TEM (transmission electron microscopy) and a dynamic Light scattering particle size analyzer, the morphology and particle size distribution of Prot-TCA/GLP-1 (Example 5) were observed.

The nanoparticles had an average size of about 150 nm and showed a relatively uniform size distribution.

(Surface Charge of Nanoparticles)

Using a zeta potential analyzer, the zeta potential of the nanoparticle produced in Example 5 was measured. As a result, the nanoparticle showed a positive zeta potential. This positive surface charge means that the negatively charged GLP-1-encoding gene is completely encapsulated in the gene delivery complex. The positive surface charge facilitates intracellular internalization of the gene delivery nanoparticle. In addition, it induces electrostatic repulsion between the particles, thereby reducing agglomeration of the particles.

(Stability of Nanoparticles)

In order to confirm the stability of the nanoparticles produced in Examples 5 and 6, gel retardation analysis was performed.

The gel retardation experiment was performed using 1% agarose gel and 1×TBE buffer solution. The gene GLP-1 encapsulated in the nanoparticles of the present invention was stained on 0.5 µg/mL EtBr (ethidium bromide) and imaged on the gel. The experiment was performed at 100 V for 30 minutes.

As a result, it was confirmed that the conjugation of GLP-1 to Prot-TCA and the conjugation of the GLP-1-encoding gene to CS-TCA were performed at a molar ratio of 1:10 or more. In particular, when the conjugation between Prot-TCA and GLP-1 in Example 5 was performed at a molar ratio of 1:150 and the conjugation between CS-TCA and GLP-1-encoding gene in Example 6 was performed at a molar ratio of 1:10, a retardation phenomenon due to condensation of the GLP-1-encoding gene was induced, and thus migration of the GLP-1-encoding gene was completely retarded. This suggests that each of Prot-TCA and CS-TCA effectively condensed the GLP-1-encoding gene, and thus the gene delivery complexes (Prot-TCA/GLP-1 and CS-TCA/GLP-1) were formed. Accordingly, the nanoparticle according to the present invention can form a complex with the gene and can be advantageously used as a gene carrier for delivering the gene.

(Stability in Serum)

In order to confirm the serum stability of the nanoparticles produced in Examples 5 and 6, an experiment was performed as follows.

Each of Prot-TCA/GLP-1 (Example 5) and CS-TCA/GLP-1 (Example 6) was stored in 20% serum at 37° C. for 48 hours, and then treated with 0.5 M of EDTA. Thereafter, 1% SDS was added in order to separate the GLP-1-encoding gene from each of Prot-TCA/GLP-1 (Example 5) and CS-TCA/GLP-1 (Example 6).

As a result, it was shown that, in comparison with the free gene GLP-1, the GLP-1-encoding gene encapsulated in each of Prot-TCA/GLP-1 (Example 5) and CS-TCA/GLP-1 (Example 6) was not degraded from the serum over 48 hours and was very stable in the serum.

(Particle Stability Against pH Conditions)

The stability of the nanoparticles according to the present invention was examined under various pH conditions.

Specifically, each of Prot-TCA/GLP-1 (Example 5) and CS-TCA/GLP-1 (Example 6) was added to three solutions having different pHs (pH 3, pH 5 and pH 7.4) similar to the pHs of the stomach, duodenum and ileum fragments of the gastrointestinal (GI) tract, and the particle size thereof was observed. As a result, it was confirmed that Prot-TCA/GLP-1 (Example 5) and CS-TCA/GLP-1 (Example 6) were all stable at pH 3 up to 24 hours.

Experimental Example 1: In Vitro Gene Expression and Transwell Studies

Using ASBT (Apical Sodium-dependent Bile Salt Transporter)-overexpressing MDCK and Caco-2 cell lines, the expression of green fluorescent protein (GFP) was observed.

4 µg of eGFP gene was loaded onto the nanoparticle for gene delivery produced in each of Examples 5 and 6, and then successful expression and green fluorescence from the cell lines were observed.

Thereafter, in order to study delivery of the gene complex in bilayer cell culture technology, a Caco-2 monolayer was cultured in the apical portion of a transwell plate, and the MDCK-ASBT cell line was cultured at the bottom portion. As a result, successful delivery of the nanoparticles was observed, suggesting that the TCA molecule functions to assist in the uptake and delivery of these gene complexes.

A GLP-1 ELISA kit that quantifies the in vitro expression of GLP-1 in response to glucose levels in medium was used, and as a result, increased expression of the GLP-1-encoding gene appeared.

Experimental Example 2: In Vivo Bio-Distribution of Complex

In order to examine the in vivo bio-distribution of the eGFP-loaded nanoparticles for gene delivery prepared in Examples 5 and 6, the following experiment was performed.

Balb/c mice were housed in wood cages and regularly provided with food and water. For 12 hours before oral administration of the therapeutic gene complex, the animals were fasted. After 12 hours of fasting, each of the gene delivery nanoparticles of Examples 5 and 6, which contained 100 µg of the eGFP gene, was administered to the animals by oral gavage. At 24 hours after administration, the animals were sacrificed, and the in vivo expression of the gene and the in vivo bio-distribution of the sample were quantified using a confocal microscope.

As a result, the gene delivery nanoparticles of the present invention showed increased expressions of the eGFP gene in the ileum and liver fragments. In addition, it could be seen that TCA conjugated to each of protamine and chitosan prevented GI (gastrointestinal) degradation of the gene and assisted in the uptake and expression of eGFP.

Experimental Example 3: In Vivo Expression of GLP-1-Encoding Gene and Regulation of Blood Glucose Level 5-week-old ZDFRs (Zucker diabetic fatty rats) were housed in wood cages and regularly provided with food and water. For 12 hours before oral administration of the gene delivery nanoparticles of Examples 5 and 6, the animals were fasted. After 12 hours of fasting, 100 µg of each of the gene delivery nanoparticles of Examples 5 and 6 were administered orally to each animal. At predetermined intervals of time from 24 hours after administration, blood was sampled from the tail vein of each animal, and the glucose level of the blood was measured. It was surprisingly confirmed that the blood glucose level was regulated to a normal blood glucose level. After 5 days, the experimental animals were sacrificed, and expressions of GLP-1 and insulin in ileum and liver fragments were analyzed using an ELISA kit. As a result, it was confirmed that, in comparison with the control group, increased expressions of the GLP-1 peptide and insulin protein appeared after oral administration of the nanoparticle for gene delivery according to the present invention.

Experimental Example 4: In Vivo Toxicity of Complex for GLP-1 Gene Delivery 4-week-old Sprague Dawley (SD) rats were housed in wood cages and regularly provided with food and water. 100 µg of each of the gene delivery nanoparticles of Examples 5 and 6 were administered orally and intravenously to each animal. Blood was sampled from the experimental animals at predetermined intervals of time for 24 hours, and complete blood content in the blood was analyzed, and expression of a biological marker that determines liver and kidney toxicities was evaluated. As a result, the gene delivery complex of the present invention showed almost no toxicity, even when it was administered at a very high concentration.

On 7 days after administration, the animals were sacrificed, and immunohistological examination of ileum and liver fragments was performed. As a result, no inflammation was observed in the tissues, and little toxicity was also observed.

Therefore, it can be seen that the gene delivery complex of the present invention is safe and nontoxic and can be used for treatment of diabetes.

Example 7: Production of Nanoparticle Comprising Protamine-Taurocholic Acid Conjugate and pDNA (Hereinafter Referred to as 'pDNA/Prot-TCA')

A protamine-taurocholic acid conjugate was produced by conjugating the hydroxyl group of taurocholic acid to the amino group of protamine using triethylamine (hereinafter referred to as TEA) and 4-nitrophenyl chloroformate (hereinafter referred to as 4-NPC).

Production of Prot-TCA

4-NPC (70 mmol) completely dissolved in 3 ml of DMF solution was added to a solution of taurocholic acid (50 mmol) in 10 ml of distilled water, and 100 μl of a TEA solution was added until the taurocholic acid solution turned completely yellow. Next, protamine (5 mmol) was added, followed by reaction at room temperature while stirring for 24 hours. After completion of the reaction, unreacted material was removed by dialysis. The dialysis was performed with distilled water through a membrane filter (1 kDa size) for 24 hours. Next, freeze-drying was performed to obtain Prot-TCA.

Production of pDNA/Prot-TCA

Each of the Prot-TCA (150 nmol to 50 nmol), prepared by the above-described experimental method, and pDNA (1 nmol), was added to HEPES buffer solution. Next, the prepared Prot-TCA solution was stirred, and at the same time, 10 μl of the HEPES buffer solution containing pDNA was added each time. After a predetermined amount of pDNA was completely added, additional stirring was performed for 10 minutes, and the reaction was finished, thereby obtaining the final product pDNA/Prot-TCA (FIG. 8).

(Experiment on pH Stability of pDNA/Prot-TCA)

In order to confirm the stability of the produced pDNA/Prot-TCA, an experiment was performed using distilled water and HEPES buffer solutions having pH 5.2, pH 1.8 and pH 7.4. In the experiment, the stabilities of pDNA/Prot-TCA and pDNA/Prot were measured by measuring the time-dependent size. Specifically, immediately after the start of the experiment and at 6, 12 and 24 hours after the start of the experiment, the pDNA/Prot-TCA solution was sampled and analyzed.

As a result, it was confirmed that pDNA/Prot-TCA showed excellent stability under the above-described conditions. This suggests that the pH stability was increased due to conjugation of taurocholic acid, a kind of bile acid. As a control, pDNA/Prot not conjugated with taurocholic acid was used. For the control, it was observed that the size showed a tendency to increase with time under the conditions of pH 5.2, pH 7.4 and distilled water, and showed a tendency to decrease with time at pH 1.8. In particular, the reason why the size showed a tendency to decrease at pH 1.8 is because protamine was weak and degraded under acidic conditions and its physical bond with pDNA was broken (Confirmation of Synthesis of pDNA/Prot-TCA Using SEM Image)

The produced pDNA/Prot-TCA was placed on a silicon wafer and then naturally dried, thereby preparing a sample to be analyzed. Analysis was performed using scanning electron microscopy at 10.0 kV and ×2,000 magnification As a result, it could be seen that the produced pDNA/Prot-TCA had a particle shape having a size of 100 nm and that all the observed particles also had a uniform size.

(Experiment on Toxicity of pDNA/Prot-TCA by Use of HCT 116 Cells)

HCT 116 cells were used to evaluate the toxicity of the produced pDNA/Prot-TCA, and an MTT assay was used for toxicity verification.

As theoretically known, it could be seen that protamine showed a survival rate of 85% or higher and that the protamine-taurocholic acid conjugate also showed a high survival rate of 80% or higher.

(Cellular Uptake Experiment Using Confocal Microscopy)

HCT 116 cells were used to examine the cellular uptake of the produced pDNA/Prot. In the experimental method, HCT 116 cells were dispensed into an 8-well plate at a concentration of $10^5$ cells/well, and then Rhodamine B-conjugated samples (pDNA/Prot and pDNA/Prot-TCA) were injected. After 2 hours of incubation, the cells were washed three times with PBS and observed using confocal microscopy.

As a result, it could be seen that pDNA/Prot-TCA had better cellular uptake ability than the control pDNA/Prot and that the cellular uptake ability was about 4-fold higher.

(Analysis of Cell Permeability of pDNA/Prot-TCA Using Caco-2 Monolayer)

In order to verify the cell permeability of pDNA/Prot-TCA, an experiment was performed by culturing Caco-2 cells as a monolayer. The experiment was performed for a total of 6 hours, and samples were collected at 10 min, 30 min, 1, 2, 4 and 6 hours and analyzed.

As a result, it could be seen that pDNA/Prot-TCA had better cell permeability than the control pDNA/Prot, suggesting that pDNA/Prot-TCA can be absorbed through small intestine in a subsequent animal experiment.

(Experiment for Analysis of In Vivo Bio-Distribution of pDNA/Prot-TCA after Oral Administration)

For an experiment for analysis of the in vivo bio-distribution of pDNA/Prot-TCA after oral administration, Rhodamine B-conjugated protamine was used and 7-week-old Balb/c mice were used. After 6 hours of fasting, the drug was administered orally to the mice, and the in vivo bio-distribution of the drug at 0.2, 0.5, 2, 6, 12 and 24 hours was determined based on fluorescence images and fluorescence levels.

As a result, it was confirmed that pDNA/Prot-TCA was absorbed through small intestine, absorbed in small intestine within a short time of less than 30 minutes, absorbed into the liver over 2 to 6 hours, and then eliminated slowly. This suggests that pDNA/Prot-TCA follows the known in vivo circulation pathway of taurocholic acid, and it was verified that the produced pDNA/Prot-TCA also neither interferes with nor impairs the in vivo uptake of taurocholic acid and maintains the original circulation pathway of taurocholic acid.

Example 8: Production of Nanoparticle Comprising Chitosan-Taurocholic Acid Conjugate and pDNA (Hereinafter Referred to as 'pDNA/CS-TCA')

Production of TCA-NPC

To conjugate TCA to chitosan, TCA (50 mmol) was dissolved in DMSO (10 mL), and then 4-NPC (200 mg) and TEA (100 µg) was added thereto, followed by reaction at room temperature for 1 hour, thereby producing TCA-NPC.

Production of CS-TCA

Chitosan (100 mg) was dissolved in distilled water, and the produced TCA-NPC (20 mg) was added thereto, followed by stirring for 24 hours. Next, unreacted material was removed by dialysis. The dialysis was performed with distilled water through a 1-kDa membrane filter for 24 hours. Next, freeze-drying was performed, thereby obtaining the final product CS-TCA.

Production of pDNA/CS-TCA

Each of CS-TCA (150 nmol to 50 nmol), produced by the above-described experimental method, and pDNA (1 nmol), was added to HEPES buffer solution. Next, the prepared CS-TCA solution was stirred, and at the same time, 10 µl of the HEPES buffer solution containing pDNA was added each time. After a predetermined amount of pDNA was completely added, additional stirring was performed for 10 minutes, and the reaction was finished, thereby obtaining the final product pDNA/CS-TCA.

(Examination of Stability of pDNA/CS-TCA by Electrophoresis Assay and Size Analysis)

The stability of pDNA/CS-TCA was examined by performing electrophoresis and measuring the size thereof, and distilled water was used as a background condition.

As a result, it was confirmed that the produced pDNA/CS-TCA was maintained in a very stable state for at least 24 hours.

(Verification of Production of pDNA/CS-TCA by Surface Charge Measurement)

A zeta potential analyzer was used to verify the production of pDNA/CS-TCA, and whether pDNA/CS-TCA would be produced was examined by measuring the surface charge (mV).

Conventional pDNA has a surface charge of −2.96 mV, and chitosan has a surface charge of 36.12 mV. When pDNA/CS-TCA was produced, it had a surface charge of 19.55 to 25.68 mV. This is because cationic chitosan completely surrounded the surface of anionic pDNA, and thus the produced pDNA/CS-TCA had a cationic surface charge. This suggests that pDNA/CS-TCA was successfully produced.

(Experiment on pH Stability of pDNA/CS-TCA)

In order to confirm the stability of the produced pDNA/CS-TCA, an experiment was performed using PBS buffer solutions having pH 5.2, pH 1.8 and pH 7.4. In the experiment, the stability of pDNA/CS-TCA was measured by measuring the time-dependent size. Specifically, immediately after the start of the experiment and at 6, 12, 18 and 24 hours after the start of the experiment, the pDNA/CS-TCA solution was sampled and analyzed.

As a result, it was confirmed that pDNA/CS-TCA showed excellent stability under the above-described conditions. This suggests that the pH stability was increased due to conjugation of taurocholic acid, a kind of bile acid.

(Experiment on Toxicity of pDNA/CS-TCA Using MDCK-ASBT Cells)

MDCK-ASBT cells were used to evaluate the toxicity of the produced pDNA/CS-TCA, and an MTT assay was used for toxicity verification.

As a result, it was confirmed that pDNA/CS-TCA showed a high survival rate of 80% or higher.

(Cellular Uptake Experiment Using Confocal Microscopy)

MDCK-ASBT cells were used to examine the cellular uptake of the produced pDNA/CS-TCA. In the experimental method, MDCK-ASBT cells were dispensed into an 8-well plate at a concentration of $10^5$ cells/well, and then Rhodamine B-conjugated samples (pDNA/chitosan and pDNA/CS-TCA) were injected. After 2 hours of incubation, the cells were washed three times with PBS and observed using confocal microscopy.

As a result, it could be seen that pDNA/CS-TCA had better cellular uptake ability than the control pDNA/chitosan and that the cellular uptake ability was about 2-fold higher.

(Analysis of Cell Permeability of pDNA/CS-TCA Using Caco-2 Monolayer)

In order to confirm the cell permeability of pDNA/CS-TCA, an experiment was performed by culturing Caco-2 cells as a monolayer. The experiment was performed for a total of 6 hours, and samples were collected at 10 min, 30 min, 1, 2, 4 and 6 hours and analyzed.

As a result, it could be seen that pDNA/CS-TCA had better cell permeability than the control pDNA/Chitosan, suggesting that pDNA/CS-TCA can be absorbed through small intestine in a subsequent animal experiment.

(Confirmation of Gene Delivery Ability of pDNA/CS-TCA by Gene Expression)

A luciferase assay was used to verify the gene expression effect of pDNA/CS-TCA. As controls, pDNA, pDNA/Chitosan and bPEI were used.

As a result, it was confirmed that pDNA/CS-TCA was 2 to 50-fold more effective than the negative controls (pDNA and pDNA/Chitosan) and had a better gene delivery effect than the positive control (bPEI).

(Experiment for Analysis of In Vivo Bio-Distribution of pDNA/CS-TCA after Oral Administration)

For an experiment for analysis of the in vivo bio-distribution of pDNA/CS-TCA after oral administration, Rhodamine B-conjugated chitosan was used and 7-week-old Balb/c mice were used. After 6 hours of fasting, the drug was administered orally to the mice, and the in vivo bio-distribution of the drug at 12 hours was determined based on fluorescence images.

As a result, it was confirmed that pDNA/CS-TCA was absorbed through small intestine, particularly ileum, and also absorbed into the liver. This suggests that pDNA/CS-TCA follows the known in vivo circulation pathway of taurocholic acid, and it was verified that the produced pDNA/Chitosan-TCA also neither interferes with nor impairs the in vivo uptake of taurocholic acid and maintains the original circulation pathway of taurocholic acid.

Example 9: Production of Nanoparticle Comprising Polyamidoamine-Taurocholic Acid Conjugate and pDNA (Hereinafter Referred to as 'pDNA/PAMAM-TCA')

Production of TCA-NPC

To conjugate TCA to chitosan, TCA (50 mmol) was dissolved in DMSO (10 mL), and then 4-NPC (200 mg) and TEA (100 µg) were added thereto, followed by reaction at room temperature for 1 hour, thereby producing TCA-NPC.

Production of PAMAM-TCA

Polyamidoamine (100 mg) was dissolved in HEPES buffer solution, and the produced TCA-NPC (20 mg) was added thereto, followed by stirring for 24 hours. Next, unreacted material was removed by dialysis. The dialysis was performed with distilled water through a 1-kDa membrane filter for 24 hours. Next, freeze-drying was performed, thereby obtaining the final product PAMAM-TCA.

Production of pDNA/PAMAM-TCA

Each of PAMAM-TCA (150 nmol to 50 nmol), produced by the above-described experimental method, and pDNA (1 nmol), was added to HEPES buffer solution. Next, the prepared MAM-TCA solution was stirred and, at the same time, 10 µl of the HEPES buffer solution containing pDNA was added each time. After a predetermined amount of pDNA was completely added, additional stirring was performed for 10 minutes, and the reaction was finished, thereby obtaining the final product pDNA/PAMAM-TCA.

Example 10: Production of Nanoparticle Comprising Poly-L-Lysine-Taurocholic Acid Conjugate and pDNA (Hereinafter Referred to as 'pDNA/PLL-TCA')

Production of TCA-NPC

To conjugate TCA to chitosan, TCA (50 mmol) was dissolved in DMSO (10 mL), and then 4-NPC (200 mg) and TEA (100 µg) were added thereto, followed by reaction at room temperature for 1 hour, thereby producing TCA-NPC.

Production of PLL-TCA

Poly-L-lysine (50 mg) was dissolved in HEPES buffer solution, and the produced TCA-NPC (20 mg) was added thereto, followed by stirring for 24 hours. Next, unreacted material was removed by dialysis. The dialysis was performed with distilled water through a 1-kDa membrane filter for 24 hours. Next, freeze-drying was performed, thereby obtaining the final product PLL-TCA.

Production of pDNA/PLL-TCA

Each of PLL-TCA (150 nmol to 50 nmol), produced by the above-described experimental method, and pDNA (1 nmol), was added to HEPES buffer solution. Next, the prepared PLL-TCA solution was stirred and, at the same time, 10 µl of the HEPES buffer solution containing pDNA was added each time. After a predetermined amount of pDNA was completely added, additional stirring was performed for 10 minutes, and the reaction was finished, thereby obtaining the final product pDNA/PLL-TCA.

Example 11: Production of Heparin Conjugated with TCA Via Disulfide Bond (Hereinafter Referred to as 'Hep-S—S-TCA')

Synthesis of Hep-S—S-TCA was started with the conjugation of heparin with cystamine. Namely, the carboxyl group of heparin was conjugated to the amino group of cystamine through EDC (1-ethyl-3-(-3-dimethylaminopropyl)carbodiimide)/NHS (N-bromosuccinimide) chemistry.

Production of Hep-S—S—NH2

Heparin (100 mg) was dissolved in 10 mL of MES buffer (50 mmol, pH 6), and stirred in a cold bath until the solution became transparent. An excessive amount of EDC (2.4 equivalents relative to heparin) was added thereto, followed by stirring for 10 minutes, after which an excessive amount of NHS (2.5 equivalents relative to EDC) was added at room temperature, followed by stirring for 10 minutes. After the carboxyl group was activated by EDC and NHS, cystamine (100 µg) was added, followed by reaction at pH 7 for 24 hours. After completion of the reaction, the reaction solution was dialyzed with double-distilled water for 24 hours and freeze-dried to obtain Hep-S—S—NH2 (FIG. 9).

Production of TCA-NPC

To conjugate TCA to activated heparin, TCA (50 mmol) was dissolved in DMSO (10 mL), and then 4-NPC (200 mg) and TEA (100 µg) were added thereto, followed by reaction at room temperature for 1 hour, thereby producing TCA-NPC (FIG. 10).

Production of Hep-S—S-TCA

Next, activated heparin (100 µg) dissolved in DMSO (10 mL) was added thereto, followed by reaction at room temperature for 24 hours. The reaction solution was dialyzed with double-distilled water through a dialysis membrane (MWCO: 1000 Da) for 48 hours while the medium was replaced every 3 hours. After dialysis, the reaction product was freeze-dried to obtain Hep-S—S-TCA (yield: 80±5%; FIGS. 11 and 12).

Hep-S—S-TCA was synthesized so as to locally release the therapeutic gene in response to intracellular glutathione, and FIGS. 9 to 11 illustrate reaction schemes for producing Hep-S—S-TCA.

Conjugation of cystamine to heparin was determined quantitatively and qualitatively by $^1$H NMR and TNBS analysis, respectively (FIG. 12). From this result, it could be seen that a TCA molecule was attached to each heparin molecule by five disulfide bonds.

Example 12: Production of Nanoparticle Comprising Heparin Conjugated with TCA Via Disulfide Bond, pDNA and Protamine (Hereinafter Referred to as pDNA/Prot/Hep-S—S-TCA')

The method of Example 11 was used in the production of Hep-S—S-TCA.

Production of pDNA/Prot

Each of protamine (150 nmol to 50 nmol) and pDNA (1 nmol) was added to HEPES buffer solution. Next, the protamine solution was stirred and, at the same time, 10 µl of the HEPES buffer solution containing pDNA was added each time. After a predetermined amount of pDNA was completely added, additional stirring was performed for 20 minutes, and the reaction was finished, thereby obtaining the final product pDNA/Prot.

Production of pDNA/Prot/Hep-S—S-TCA

Each of Hep-S—S-TCA (20 mg) and pDNA/Prot was added to HEPES buffer solution Next, the Hep-S—S-TCA solution was stirred and, at the same time, 1 ml of the HEPES buffer solution containing pDNA/Prot was added each time. After a predetermined amount of pDNA/Prot was completely added, additional stirring was performed for 30 minutes, and the reaction was finished, thereby obtaining the final product pDNA/Prot/Hep-S—S-TCA.

(Confirmation of Production of pDNA/Prot by Electrophoresis Assay)

An electrophoresis assay was used to confirm the production of pDNA/Prot, and HEPES buffer solution was used as a background condition. Comparison was performed between weight ratios of 1:0.5, 1, 2, 3, 4 and 6, thereby determining an optimal condition.

As a result, it was confirmed that the produced pDNA/Prot was very stably produced, and it was perfectly produced when a weight ratio of at least 1:2 was used.

(Confirmation of Production of pDNA/Prot by Particle Size Analysis and Surface Charge Analysis)

Particle size analysis and surface charge analysis were used to confirm the production of pDNA/Prot, and HEPES buffer solution was used as a background condition. Comparison was performed between weight ratios of 1:0.5, 1, 2, 3, 4 and 6, thereby determining an optimal condition.

As a result, it was confirmed that the produced pDNA/Prot was very stably produced, and a weight ratio of 1:3 was an optimal condition in the production of pDNA/Prot.

(Confirmation of Production of pDNA/Prot/Hep-S—S-TCA by Electrophoresis Assay and Particle Size Analysis)

Electrophoresis assay and particle size analysis were used to confirm the production of pDNA/Prot/Hep-S—S-TCA, and HEPES buffer solution was used as a background condition. Comparison was performed between weight ratios of 1:3 and 4.5, thereby determining an optimal condition.

As a result, it was confirmed that the produced pDNA/Prot/Hep-S—S-TCA was very stably produced, and it was perfectly produced when a weight ratio of at least 1:3 was used.

(Confirmation of Synthesis of pDNA/Prot/Hep-S—S-TCA Using TEM Image)

The produced pDNA/Prot/Hep-S—S-TCA was placed on a silicon wafer, and then naturally dried, thereby preparing a sample to be analyzed. The sample was analyzed using transmission electron microscopy.

As a result, it could be seen that the produced pDNA/Prot/Hep-S—S-TCA had a particle shape having a size of 100 nm. In addition, a coating layer of Hep-S—S-TCA on the surface was observed, indicating that pDNA/Prot/Hep-S—S-TCA was perfectly produced. Furthermore, it was confirmed that all the observed particles also had a uniform size.

(Measurement of Encapsulation Rate of Gene in pDNA/Prot/Hep-S—S-TCA)

An electrophoresis assay was used to measure the encapsulation rate of the gene in pDNA/Prot/Hep-S—S-TCA, and the encapsulation rate was measured by measuring the amount of DNA separated for electrophoresis.

As a result, it was confirmed that a weight ratio of 1:6 showed an encapsulation rate of 70%, which was the highest encapsulation rate, and that a weight ratio of 1:3 showed an encapsulation rate of about 15%. Although a weight ratio of 1:6 showed the highest encapsulation rate, the optimized weight ratio for gene delivery was set to 1:3 as mentioned above in the experiment for confirming the production of pDNA/Prot/Hep-S—S-TCA by the electrophoresis assay and particle size analysis.

(Confirmation of Stability of pDNA/Prot/Hep-S—S-TCA by Electrophoresis Assay)

An electrophoresis assay was used to confirm the stability of pDNA/Prot/Hep-S—S-TCA, and an HEPES buffer solution containing DNAse, a pDNA degrading enzyme, was used as a background condition.

As a result, it was confirmed that the produced pDNA/Prot/Hep-S—S-TCA effectively protected pDNA from the pDNA degrading enzyme DNAse and was maintained in a very stable state.

(Cellular Uptake Experiment Using Confocal Microscopy)

MDCK-ASBT cells were used to examine the cellular uptake of the produced pDNA/Prot/Hep-S—S-TCA. In the experimental method, MDCK-ASBT cells were dispensed into an 8-well plate at a concentration of $10^5$ cells/well, and then Rhodamine B-conjugated samples (pDNA/Prot and pDNA/Prot/Hep-S—S-TCA) were injected. After 2 hours of incubation, the cells were washed three times with PBS and observed using confocal microscopy.

As a result, it was confirmed that although pDNA/Prot used as the control also showed slight uptake ability due to its cationic surface charge, the produced pDNA/Prot/Hep-S—S-TCA had better cellular uptake ability than the control pDNA/Prot.

(Cell Expression Experiment Using Confocal Microscopy)

HepG2 cells were used to evaluate the effect of the produced pDNA/Prot/Hep-S—S-TCA on intracellular expression. In the experimental method, HepG2 cells were dispensed into an 8-well plate at a concentration of $10^5$ cells/well, and then eGFP-conjugated samples (pDNA/Prot and pDNA/Prot/Hep-S—S-TCA) were injected. After 24 hours of incubation, the cells were washed three times with PBS and observed using confocal microscopy.

As a result, it was confirmed that the produced pDNA/Prot/Hep-S—S-TCA had green fluorescence by successfully delivering the eGFP gene and that the intensity of the fluorescence was significantly higher than that of the control pDNA/Prot.

(Experiment on Toxicity of pDNA/Prot/Hep-S—S-TCA by Use of MDCK-ASBT Cells)

MDCK-ASBT cells were used to evaluate the toxicity of the produced pDNA/Prot/Hep-S—S-TCA, and an MTT assay was used for toxicity verification.

As a result, it was confirmed that Hep-S—S-TCA showed a survival rate of 90% or higher and pDNA/Prot/Hep-S—S-TCA also showed a high survival rate of 90% or higher.

(Examination of Cell Permeability of pDNA/Prot/Hep-S—S-TCA by Use of Caco-2 Monolayer)

To confirm the cell permeability of pDNA/Prot/Hep-S—S-TCA, an experiment was performed by culturing Caco-2 cells as a monolayer. The experiment was performed for a total of 6 hours, and samples were collected at 10 min, 30 min, 1, 2, 4 and 6 hours and analyzed.

As a result, it was confirmed that pDNA/Prot/Hep-S—S-TCA had lower cell permeability than the control pDNA/Prot/CSA-TCA and that the cell permeability was similar to that of pDNA/Prot. This suggests that taurocholic acid is separated in Caco-2 cells by the disulfide bond (—S—S—) and that only taurocholic acid permeates the cells and pDNA/Prot/Hep is accumulated in the cells.

(Experiment for Analysis of In Vivo Bio-Distribution of pDNA/Prot/Hep-S—S-TCA after Oral Administration)

For an experiment for analysis of the in vivo bio-distribution of pDNA/Prot/Hep-S—S-TCA after oral administration, Rhodamine B-conjugated protamine was used and 7-week-old Balb/c mice were used. After 6 hours of fasting, the drug was administered orally or intravenously to the mice, and the in vivo bio-distribution of the drug at 6 hours was determined based on fluorescence images of tissue and cells.

As a result, it was confirmed that pDNA/Prot/Hep-S—S-TCA was absorbed through the small intestine, particularly the ileum, and was also slightly absorbed into the liver. This suggests that pDNA/Prot/Hep-S—S-TCA follows the known in vivo circulation pathway of taurocholic acid up to the small intestine and that the disulfide bond (—S—S—) is separated in the small intestine and the produced pDNA/Prot/Hep is accumulated in the small intestine outside the circulation pathway of taurocholic acid.

Example 13: Production of Chitosan Conjugated with TCA by Disulfide Bond (Hereinafter Referred to as 'CS—S—S-TCA')

Production of Chitosan-S—S—COOH

Chitosan (100 mg) was dissolved in 10 mL of MES buffer (50 mmol, pH 6), and stirred in a cold bath until the solution became transparent. An excessive amount of EDC (5 equivalents relative to chitosan) was added thereto, followed by stirring for 10 minutes, after which an excessive amount of NHS (2.5 equivalents relative to EDC) was added at room temperature, followed by stirring for 10 minutes. After the carboxyl group was activated by EDC and NHS, cysteine (500 µg) was added, followed by reaction at pH 7 for 24 hours. After completion of the reaction, the reaction solution was dialyzed with double-distilled water for 24 hours and freeze-dried to obtain Chitosan-S—S—COOH.

Production of TCA-NH2

To conjugate TCA to activated Chitosan-S—S—COOH, TCA (50 mmol) was dissolved in DMSO (10 mL), and then 4-NPC (200 mg) and TEA (100 µg) were added thereto, followed by reaction at room temperature for 1 hour, thereby producing TCA-NPC.

Next, the produced TCA-NPC (100 mg) was completely dissolved in DMF, and 30 µl of 4-MMP was added thereto and reacted for 4 hours. Thereafter, 1 ml of ethylenediamine was added to the reaction solution and reacted for 16 hours, thereby producing TCA-NH$_2$.

Production of CS—S—S-TCA

Thereafter, the activated Chitosan-S—S—COOH (100 µg) dissolved in DMSO (10 mL) was added, followed by reaction at room temperature for 24 hours. The reaction solution was dialyzed with double-distilled water at pH 7 through a dialysis membrane (MWCO: 1000 Da) for 24 hours while the medium was replaced every 3 hours. After dialysis, the reaction product was freeze-dried to obtain CS—S—S-TCA (yield: 50%; FIGS. 13 and 14).

Example 14: Production of Nanoparticle Comprising Chitosan, Conjugated with TCA Via Disulfide Bond, and pDNA (Hereinafter Referred to as 'pDNA/CS—S—S-TCA')

Each of CS—S—S-TCA (20 nmol) and pDNA (1 nmol) was added to HEPES buffer solution. Next, the prepared CS—S—S-TCA solution was stirred and, at the same time, 10 µl of the HEPES buffer solution containing pDNA was added each time. After a predetermined amount of pDNA was completely added, additional stirring was performed for 10 minutes, and the reaction was finished, thereby obtaining the final product pDNA/CS—S—S-TCA.

(Confirmation of Production of pDNA/CS—S—S-TCA by Electrophoresis Assay and Particle Size Analysis)

Electrophoresis assay and particle size analysis were performed to confirm the production of pDNA/CS—S—S-TCA, and HEPES buffer solution was used as a background condition. Comparison was performed between weight ratios of 1:3 and 4.5, thereby determining an optimal condition.

The results of the electrophoresis assay indicated that the produced pDNA/CS—S—S-TCA was very stably produced and it was perfectly produced when a weight ratio of at least 1:5 was used. In addition, based on the change in the particle size, the optimal weight ratio was set to 1:50.

(Experiment on pH Stability of pDNA/CS—S—S-TCA)

In order to confirm the stability of the produced pDNA/CS—S—S-TCA, an experiment was performed using PBS buffer solutions having pH 5.2, pH 1.8 and pH 7.4. In the experiment, the stability of pDNA/CS—S—S-TCA was measured by measuring the time-dependent size. Specifically, immediately after the start of the experiment and at 6, 12, 18 and 24 hours after the start of the experiment, the pDNA/CS—S—S-TCA solution was sampled and analyzed.

As a result, it was confirmed that pDNA/CS—S—S-TCA showed excellent stability under the above-described conditions. This suggests that the pH stability was increased due to conjugation of taurocholic acid, a kind of bile acid.

(Experiment on Toxicity on pDNA/CS—S—S-TCA by Use of MDCK-ASBT Cells)

MDCK-ASBT cells were used to evaluate the toxicity of the produced pDNA/CS—S—S-TCA, and an MTT assay was used for toxicity verification.

As a result, it was confirmed that pDNA/CS—S—S-TCA showed a high survival rate of 90% or higher.

(Cellular Uptake Experiment Using Confocal Microscopy)

MDCK-ASBT cells were used to examine the cellular uptake of the produced pDNA/CS—S—S-TCA. In the experimental method, MDCK-ASBT cells were dispensed into an 8-well plate at a concentration of $10^5$ cells/well, and then Rhodamine B-conjugated samples (pDNA/Chitosan and pDNA/CS—S—S-TCA) were injected. After 2 hours of incubation, the cells were washed three times with PBS and observed using confocal microscopy.

As a result, it was confirmed that although pDNA/Chitosan used as the control also showed slight uptake ability due to its cationic surface charge, the produced pDNA/CS—S—S-TCA had better cellular uptake ability than the control pDNA/Chitosan.

(Examination of Cell Permeability of pDNA/CS—S—S-TCA by Use of Caco-2 Monolayer)

To confirm the cell permeability of pDNA/CS—S—S-TCA, an experiment was performed by culturing Caco-2 cells as a monolayer. The experiment was performed for a total of 6 hours, and samples were collected at 10 min, 30 min, 1, 2, 4 and 6 hours and analyzed.

As a result, it was confirmed that pDNA/CS—S—S-TCA had lower cell permeability than the control pDNA/CS-TCA and that the cell permeability was similar to that of pDNA/Chitosan. This suggests that taurocholic acid is separated in Caco-2 cells by the disulfide bond (—S—S—) and that only taurocholic acid permeates the cells and pDNA/CS is accumulated in the Caco-2 cells.

(Experiment for Analysis of In Vivo Bio-Distribution of pDNA/CS—S—S-TCA after Oral Administration)

For an experiment for analysis of the in vivo bio-distribution of pDNA/CS—S—S-TCA after oral administration, Rhodamine B-conjugated chitosan was used and 7-week-old Balb/c mice were used. After 6 hours of fasting, the drug was administered orally to the mice, and the in vivo bio-distribution of the drug at 6 hours was determined based on fluorescence images.

As a result, it was confirmed that pDNA/CS—S—S-TCA was absorbed through the small intestine, particularly the ileum, and was also slightly absorbed into the liver. This suggests that pDNA/Prot/Hep-S—S-TCA follows the known in vivo circulation pathway of taurocholic acid up to the small intestine and that the disulfide bond (—S—S—) is separated in the small intestine and the produced pDNA/Chitosan is accumulated in the small intestine outside the circulation pathway of taurocholic acid.

Example 15: Production of Protamine Conjugated with TCA Via Disulfide Bond (Hereinafter Referred to as 'Prot-S—S-TCA')

Production of Prot-S—S—NH2

Cysteine (10 mmol) was dissolved in 10 mL of MES buffer (50 mmol, pH 6), and stirred in a cold bath until the solution became transparent. An excessive amount of EDC (2.4 equivalents relative to cysteine) was added thereto, followed by stirring for 10 minutes, after which an excessive amount of NHS (2.5 equivalents relative to EDC) was added at room temperature, followed by stirring for 10 minutes.

After the carboxyl group was activated by EDC and NHS, protamine (150 mmol) was added, followed by reaction at pH 7 for 24 hours. After completion of the reaction, the reaction solution was dialyzed with double-distilled water for 24 hours and freeze-dried to obtain Prot-S—S—NH2.

Production of Prot-S—S-TCA

To conjugate TCA to activated protamine, TCA (50 mmol) was dissolved in DMSO (10 mL), and then 4-NPC (200 mg) and TEA (100 µg) were added thereto, followed by addition of activated protamine (100 nmol). Next, the mixture was allowed to react at room temperature for 1 hour, thereby producing Prot-S—S-TCA (FIG. 15).

Example 16: Production of Nanoparticle Comprising Protamine, Conjugated with TCA by Disulfide Bond, and pDNA (Hereinafter Referred to as 'pDNA/Prot-S—S-TCA')

Each of Prot-S—S-TCA (200 µg) and pDNA (1 µg) was added to HEPES buffer solution. Next, the prepared Prot-S—S-TCA solution was stirred and, at the same time, 10 µl of the HEPES buffer solution containing pDNA was added each time. After a predetermined amount of pDNA was completely added, additional stirring was performed for 10 minutes, and the reaction was finished, thereby obtaining the final product pDNA/Prot-S—S-TCA (yield: 80%; FIG. 16).

(Confirmation of Synthesis of Prot-S—S-TCA by TNBSA Assay and Surface Charge Measurement)

A TNBSA assay was used to confirm the synthesis of Prot-S—S-TCA. More specifically, the number of amino groups consumed, that is, the rate of conjugation of TCA, was measured by quantifying the number of amino groups of protamine. In addition, a zeta potential analyzer was used to measure the surface charge.

As a result, it was confirmed that as the feed ratio of taurocholic acid to protamine increased, the number of amino groups of the protamine decreased, and thus the surface charge also decreased. Such changes appeared at a feed ratio of up to 1:15, and no significant changes appeared after a feed ratio of 1:15. This suggests that taurocholic acid was effectively conjugated to protamine and that the optimal feed ratio is 1:15.

(Confirmation of Production of pDNA/Prot-S—S-TCA by Electrophoresis Assay, Particle Size Analysis and Surface Charge Analysis)

Electrophoresis assay, particle size analysis and surface charge measurement were performed to confirm the production of pDNA/Prot-S—S-TCA, and HEPES buffer solution was used as a background condition. Comparison was performed between weight ratios of 1:5, 25, 50, 100, 150 and 200, thereby determining an optimal condition.

The results of the electrophoresis assay indicated that the produced pDNA/Prot-S—S-TCA was very stably produced and it was perfectly produced when a weight ratio of at least 1:5 was used. In addition, based on the change in the particle size and on the surface charge value, the optimal weight ratio was set to 1:200.

(Experiment on pH Stability of pDNA/Prot-S—S-TCA)

In order to confirm the stability of the produced pDNA/Prot-S—S-TCA, an experiment was performed using PBS buffer solutions having pH 5.2, pH 1.8 and pH 7.4. In the experiment, the stability of pDNA/Prot-S—S-TCA was measured by measuring the time-dependent size. Specifically, immediately after the start of the experiment and at 6, 12 and 24 hours after the start of the experiment, the pDNA/Prot-S—S-TCA solution was sampled and analyzed.

As a result, it was confirmed that pDNA/Prot-S—S-TCA showed excellent stability under the above-described conditions. This suggests that the pH stability was increased due to conjugation of taurocholic acid, a kind of bile acid.

(Experiment on Toxicity of pDNA/Prot-S—S-TCA by Use of MDCK-ASBT Cells)

MDCK-ASBT cells were used to evaluate the toxicity of the produced pDNA/Prot-S—S-TCA, and an MTT assay was used for toxicity verification.

As a result, it was confirmed that pDNA/Prot-S—S-TCA showed a high survival rate of 90% or higher.

(Cellular Uptake Experiment Using Confocal Microscopy)

MDCK-ASBT cells were used to examine the cellular uptake of the produced pDNA/Prot-S—S-TCA. In the experimental method, MDCK-ASBT cells were dispensed into an 8-well plate at a concentration of $10^5$ cells/well, and then Rhodamine B-conjugated samples (pDNA/Prot and pDNA/Prot-S—S-TCA) were injected. After 2 hours of incubation, the cells were washed three times with PBS and observed using confocal microscopy.

As a result, it was confirmed that although pDNA/Prot used as the control also showed slight uptake ability due to its cationic surface charge, the produced pDNA/Prot-S—S-TCA had better cellular uptake ability than the control pDNA/Prot.

(Examination of Cell Permeability of pDNA/Prot-S—S-TCA by Use of Caco-2 Monolayer)

To confirm the cell permeability of pDNA/Prot-S—S-TCA, an experiment was performed by culturing Caco-2 cells as a monolayer. The experiment was performed for a total of 6 hours, and samples were collected immediately after the start of the experiment and at 10 min, 30 min, 1, 2, 4 and 6 hours and analyzed.

As a result, it was confirmed that pDNA/Prot-S—S-TCA had lower cell permeability than the control pDNA/Prot-TCA and that the cell permeability value was similar to that of pDNA/Prot. This suggests that taurocholic acid is separated in Caco-2 cells by the disulfide bond (—S—S—) and that only taurocholic acid permeates the cells, and pDNA/Prot-SH is accumulated in the Caco-2 cells, unlike pDNA/Prot.

(Confirmation of Gene Delivery Ability of Produced pDNA/Prot-S—S-TCA by Gene Expression)

A luciferase assay was used to verify the gene expression effect of pDNA/Prot-S—S-TCA. As controls, pDNA, Prot, Prot-TCA and bPEI were used.

As a result, it was confirmed that pDNA/Prot-S—S-TCA was 2- to 10-fold more effective than the negative controls (pDNA, Prot and Prot-TCA) and had a gene delivery effect similar to that of the positive control bPEI.

(Experiment for Analysis of In Vivo Bio-Distribution of pDNA/Prot-S—S-TCA after Oral Administration)

For an experiment for analysis of the in vivo bio-distribution of pDNA/Prot-S—S-TCA after oral administration, Rhodamine B-conjugated protamine was used and 7-week-old Balb/c mice were used. After 6 hours of fasting, the drug was administered orally to the mice, and the in vivo bio-distribution of the drug at 6 hours was determined based on fluorescence images.

As a result, it was confirmed that pDNA/Prot-S—S-TCA was absorbed through the ileum, and was not absorbed into the liver. This suggests that pDNA/Prot-S—S-TCA follows the known in vivo circulation pathway of taurocholic acid up to the small intestine and that the disulfide bond (—S—S—) is separated in the small intestine and the produced pDNA/Prot is accumulated in the small intestine outside the circulation pathway of taurocholic acid. As evidence, it can be seen that Prot-TCA also showed a high uptake rate in the liver after passage through the small intestine.

Example 17: Production of Hyaluronic Acid-TCA Conjugate (HA-TCA)

TCA was initially aminated in order to induce conjugation with HA. Synthesis of aminated TCA is as follows.

Production of TCA-NH2

At 0° C., TCA (1 mmol) was dissolved in DMF (dimethylformamide) (5 mL) and stirred until the solution became transparent. TEA (6 mmol) and 4-NPC (5 mmol) were sequentially added thereto, followed by reaction at 0° C. for 1 hours, after which the reaction solution was further stirred at room temperature for 6 hours. Then, the reaction solution was centrifuged at 5000 rpm, and the pellets were dispersed in ethyl acetate (20 mL), transferred to a separatory funnel, and extracted with the same amount of double-distilled water. The aqueous layer was collected, and the remaining organic solvent was removed using a rotary evaporator. The residue was freeze-dried for 48 hours, thereby obtaining TCA-NPC.

The formed TCA-NPC (1 mmol) was dissolved in DMF (5 mL), and then 4-MMP (4-mercapto-4-methylpentan-2-one) (2 mmol) was added thereto, followed by stirring at 50° C. for 60 minutes. Thereafter, ethylene diamine (100 mmol) was added dropwise to the solution, followed by reaction at room temperature for 16 hours. An excessive amount of acetone was added to the solution, and the produced precipitate was filtered and then freeze-dried for 48 hours, thereby obtaining TCA-NH2 (FIG. 17).

Production of HA-TCA

Conjugation of TCA with HA (hyaluronic acid) was performed by EDC/NHS chemistry. The carboxyl group of HA was initially treated with EDC (200 mg) at pH 4 and at 4° C. for 15 minutes. Then, NHS (100 μg) was added to HA and stirred for 10 minutes. Next, TCA-NH2 (100 μg) was added, followed by reaction at pH 7 and at room temperature for 7 hours. After completion of the reaction, the reaction solution was dialyzed with double-distilled water through a dialysis membrane (MWCO: 1000 Da) for 24 hours, and then freeze-dried for 48 hours, thereby obtaining HA-TCA (yield: 10%; FIG. 18).

Example 18: Production of Heparin-TCA Conjugate (Hep-TCA)

Hep-TCA was produced in the same manner as described in Example 17, except that Hep was used instead of HA.

Amination of TCA helped form a stable amide bond between TCA and HA or Hep. As shown in FIG. 18, the results of $^1$H NMR analysis indicated that the peak of amide bond conjugation between TCA and HA was detected at δ 8 ppm TNBS analysis confirmed that TCA was successfully aminated. These results indicate that each TCA molecule has a single amino group in the backbone thereof. Conjugation of Hep or HA to TCA was confirmed by $^1$H NMR analysis (FIG. 18). From the peaks around 1.0 to 1.5 ppm, the presence of TCA moieties was confirmed, and from the peaks around 3.5 to 3.9 ppm, the presence of HA moieties was confirmed. In addition, from the new peak at 8 ppm, it was confirmed that a stable amide bond between TCA and HA was formed.

To quantify the number of TCA molecules conjugated to Hep or HA, sulfate assay was performed. A subsequent experiment was performed with HA-TCA or Hep-TCA in which Hep or HA and TCA were conjugated at a ratio of 1:5. Additionally, these conjugates showed a negative zeta potential.

Example 19: Production of Prot/GLP-1/HA-TCA

Prot (1 mg/mL) dissolved in 10 mM HEPES buffer (pH 7.4) was used as a stock solution. A GLP-1 gene solution was prepared by dissolving GLP-1-encoding gene (7.780 mg) in 10 mM HEPES buffer (pH 7.4) (1.922 mL). Under gentle vortexing, the GLP-1 gene solution was added dropwise to the stock Prot solution, thereby preparing a Prot/GLP-1 ionic complex solution. The Prot/GLP-1 ionic complex showed a positive zeta potential and a strong interaction when the molar ratio of Prot:GLP-1 was 1:20.

Under gentle vortexing, the Prot/GLP-1 ionic complex was added to an aqueous solution of HA-TCA at 1:1 (v/v), incubated at room temperature for 30 minutes, and then freeze-dried to obtain prot/GLP-1/HA-TCA (yield: 20%).

Example 20: Production of Prot/GLP-1/Hep-TCA prot/GLP-1/Hep-TCA was obtained in the same manner as described in Example 19, except that Hep was used instead of HA.

Prot/GLP-1 ionic complexes having different molar ratios between GLP-1 and Prot were prepared. A gel retardation experiment showed that the GLP-1-encoding gene was conjugated to Prot at a molar ratio of 1:20.

It was confirmed that the prot/GLP-1 ionic complex was stable in serum and that even when the Prot/GLP-1 ionic complex was coated with Hep-TCA or HA-TCA, the Prot/GLP-1 ionic complex was still stable in serum without losing its structural stability. In addition, TEM analysis showed that when the Prot/GLP-1 ionic complex was coated with Hep-TCA or HA-TCA, the particle size increased from 185 nm to 235 nm. In addition, after the Prot/GLP-1 gene complex was coated with Hep-TCA or HA-TCA, a transparent coating shell was observed in a TEM micrograph.

The stability of the particles was examined under various pH conditions. Specifically, the particles were added to three solutions having different pHs (pH 3, pH 5 and pH 7.4) similar to the pHs of the stomach, duodenum and ileum fragments of the gastrointestinal (GI) tract, and the particle size was observed. As a result, it was confirmed that the prot/GLP-1 ionic complex was unstable at pH 3, but the prot/GLP-1 gene complex coated with a polysaccharide-TCA polymer such as Hep-TCA or HA-TCA showed improved particle stability due to coating of the polysaccharide-TCA polymer such as Hep-TCA or HA-TCA and was stable at pH 3 up to 24 hours. This suggests that the particles are stable after being coated with the polysaccharide-TCA polymer.

Experimental Example 7: In Vitro Gene Expression and Transwell Studies

Using ASBT (Apical Sodium-dependent Bile Salt Transporter)-overexpressing MDCK and Caco-2 cell lines, the expression of green fluorescent protein (GFP) was observed.

4 μg of eGFP gene was loaded onto the gene delivery nanoparticle produced in each of Examples 19 and 20, and then successful expression and green fluorescence from the cell lines were observed.

Thereafter, in order to study delivery of the gene complex in bilayer cell culture technology, a Caco-2 monolayer was cultured in the apical portion of a transwell plate, and the MDCK-ASBT cell line was cultured in the bottom portion. Delivery of Prot/GLP-1/HA-TCA (Example 19) and Prot/GLP-1/Hep-TCA (Example 20) coated with HA-TCA and Hep-TCA, respectively, was analyzed. In the Caco-2 monolayer, the minimum expression of eGFP from Prot/GLP-1/HA-TCA (Example 19) and Prot/GLP-1/Hep-TCA (Example 20) was observed. This suggests that the shell plays an important role in release of the targeting gene.

A GLP-1 ELISA kit that quantifies the in vitro expression of GLP-1 in response to glucose levels in medium was used, and as a result, increased expression of the GLP-1-encoding gene appeared.

Experimental Example 8: In Vivo Bio-Distribution of Prot/eGFP/Polysaccharide-TCA Gene Complex In order to examine the in vivo bio-distribution of the eGFP-loaded Prot/GLP-1/HA-TCA (Example 19) and Prot/GLP-1/Hep-TCA (Example 20), the following experiment was performed.

Balb/c mice were housed in wood cages and regularly provided with food and water. For 12 hours before oral administration of the therapeutic gene complex, the animals were fasted. After 12 hours of fasting, each sample containing 100 µg of the eGFP gene was administered to the animals by oral gavage. At 24 hours after administration, the animals were sacrificed, and the in vivo expression of the gene and the in vivo bio-distribution of the sample were quantified using a confocal microscope.

As a result, the gene delivery complex of the present invention showed increased expressions of the eGFP gene in the ileum and liver fragments due to HA-TCA or Hep-TCA.

Experimental Example 9: In Vivo Expression of GLP-1-Encoding Gene and Regulation of Blood Glucose Level 5-week-old ZDFRs (Zucker diabetic fatty rats) were housed in wood cages and regularly provided with food and water. For 12 hours before oral administration of the therapeutic gene complex, the animals were fasted. After 12 hours of fasting, 100 µg of each of Prot/GLP-1/HA-TCA (Example 19) and Prot/GLP-1/Hep-TCA (Example 20) was administered orally to the animals. At predetermined intervals of time from 24 hours after administration, blood was sampled from the tail vein of each animal, and the glucose level of the blood was measured. It was surprisingly confirmed that the blood glucose level was regulated to a normal blood glucose level. After 5 days, the experimental animals were sacrificed, and expressions of GLP-1 and insulin in different tissues were analyzed using an ELISA kit. As a result, it was confirmed that, in comparison with the control group, increased expressions of the GLP-1 peptide and insulin protein appeared after oral administration of the GLP-1-loaded polysaccharide-TCA gene complexes.

Experimental Example 10: In Vivo Toxicity of Bile Acid Mediated Non-Viral Vectors 4-week-old Sprague Dawley (SD) rats were housed in wood cages and regularly provided with food and water. 100 µg of each of the gene delivery nanoparticles of the present invention, that is, prot/GLP-1/HA-TCA (Example 19) and prot/GLP-1/Hep-TCA (Example 20), were administered orally and intravenously to each animal at different concentrations. Blood was sampled from the experimental animals at predetermined intervals of time, and complete blood content in the blood was analyzed, and expression of a biological marker that determines liver and kidney toxicities was evaluated. As a result, the gene delivery nanoparticle of the present invention showed almost no toxicity, even when it was administered at a very high concentration.

On 7 days after administration, the animals were sacrificed, and immunohistological examination of ileum and liver fragments was performed. As a result, no inflammation was observed in the tissues, and little toxicity was also observed.

Therefore, it can be seen that the gene delivery nanoparticle of the present invention is safe and nontoxic and can be used for treatment of diabetes.

As describe above, although the embodiments of the present invention have been described in detail, those skilled in the field to which the present invention pertains will appreciate that the present invention may be modified in various forms without departing from the spirit and scope of the present invention as defined to the appended claims. Accordingly, modifications of the foregoing embodiments of the present invention may be made without departing from the scope of the present invention

INDUSTRIAL APPLICABILITY

The nanoparticle for gene delivery according to the present invention is a novel oral gene delivery system capable of regulating blood glucose levels in biological systems and insulin secretion in response to ingested meals, and comprises: an ionic polymer conjugated with bile acid or a bile acid derivative; and a gene.

The nanoparticle for gene delivery according to the present invention is a nanoparticle surface-modified with bile acid or its derivative, wherein an ionic complex comprising a negatively charged gene encapsulated in a cationic polymer due to the electrostatic interaction between the negatively charged gene and the cationic polymer is present in the core of the nanoparticle and wherein the bile acid or bile acid derivative conjugated to the cationic polymer is located on the surface of the nanoparticle while having a hydrophilic anionic group.

Furthermore, the nanoparticle for gene delivery according to the present invention is a nanoparticle surface-modified with bile acid or its derivative, wherein an ionic complex comprising a negatively charged gene encapsulated in a cationic polymer due to the electrostatic interaction between the negatively charged gene and the cationic polymer is present in the core of the nanoparticle and wherein the cationic polymer of the ionic complex, and the anionic polymer conjugated with the bile acid or bile acid derivative having a hydrophilic anionic group, are conjugated to each other by electrostatic interaction, and thus the bile acid or bile acid derivative conjugated to the anionic polymer is located on the surface of the nanoparticle while having a hydrophilic ionic group.

Accordingly, the nanoparticle for gene delivery according to the present invention protects against gastric acid through direct physical bonding between the cationic polymer and the gene, may be safely delivered to small intestine cells, and may also be used as a targeting nanoparticle that enables the GLP-1 gene to be expressed only in L-cells in the small intestine.

When the nanoparticle surface-modified with bile acid or its derivative according to the present invention was used to deliver a therapeutic gene to a target cell, it easily delivered the gene through intestinal mucosa and, at the same time, was very stable in the gastrointestinal tract due to the ionic complex present in the core of the nanoparticle. This suggests that the nanoparticle for gene delivery according to the present invention is very suitable for oral administration.

The bile acid located on the surface of the nanoparticle according to the present invention can inhibit gastrointestinal (GI) degradation of the nanoparticle, and absorb the bile acid receptor ASBT (apical sodium bile acid transporter) receptor of intestinal cell membrane in the small intestine ileum, thereby delivering the therapeutic gene into cells, and thus the nanoparticle can exhibit increased gene expression.

In particular, when the therapeutic gene used is GLP-1, a GLP-1 peptide, a GLP-1 variant, a GLP-1 derivative, a GLP-1 agonist, liraglutide or exendin-4, the bile acid located on the surface of the nanoparticle according to the present invention and the cationic polymer are separated by the enzyme glutathione of intestinal cells and pH and enter portal vein, and the separated therapeutic gene is delivered only to the nucleus of intestinal cells and expresses a large amount of the GLP-1, GLP-1 peptide, GLP-1 variant, GLP-1 derivative, GLP-1 agonist, liraglutide or exendin-4, thereby efficiently exhibiting diabetic therapeutic efficacy. Accordingly, the nanoparticle for gene delivery according to the present invention, when administered orally to diabetic mouse models, can exhibit blood glucose-lowering effects by secreting insulin while successfully expressing GLP-1, a GLP-1 peptide, a GLP-1 variant, a GLP-1 derivative, a GLP-1 agonist, liraglutide or exendin-4, thereby effectively preventing or treating diabetes, particularly type 2 diabetes.

[Sequence List Text]

SEQ ID NO 1: GLP-1-Encoding Sequence (DNA Sequence)

The invention claimed is:

1. A nanoparticle for gene delivery, comprising:
    an anionic polymer conjugated via a disulfide bond with a bile acid or a bile acid derivative; and a nucleic acid molecule encoding a gene,
    wherein the bile acid or bile acid derivative is selected from the group consisting of deoxycholic acid, taurodeoxycholic acid, taurocholic acid (TCA), glycocholic acid, and glycochenodeoxycholic acid, wherein the bile acid or bile acid derivative is located on the surface of the nanoparticle,
    wherein the anionic polymer is selected from the group consisting of heparin, hyaluronic acid, and chondroitin sulfate,
    wherein the nucleic acid molecule encoding a gene is encapsulated in a cationic polymer due to electrostatic interaction, and wherein the cationic polymer is selected from the group consisting of chitosan, glycol chitosan, protamine, poly-L-lysine (PLL), and polyamidoamine (PAMAM).

2. The nanoparticle for gene delivery according to claim 1, wherein the bile acid or bile acid derivative is taurocholic acid (TCA).

3. The nanoparticle for gene delivery according to claim 1, wherein the nucleic acid molecule encoding a gene is at least one selected from the group consisting of single-stranded or double-stranded DNA (deoxyribonucleic acid), single-stranded or double-stranded RNA (ribonucleic acid), plasmid DNA (pDNA), antisense oligonucleotides, ribozymes, and catalytic RNA.

4. The nanoparticle for gene delivery according to claim 3, wherein the nucleic acid molecule encoding a gene is at least one selected from the group consisting of a gene encoding glucagon-like peptide-1 (GLP-1), a gene encoding a GLP-1 variant, a gene encoding a GLP-1 derivative, a gene encoding a GLP-1 agonist, a gene encoding liraglutide, and a gene encoding exendin-4.

5. The nanoparticle for gene delivery according to claim 1, wherein the bile acid or bile acid derivative and the anionic polymer are conjugated to each other at a molar ratio of 1:1 to 1:300.

6. The nanoparticle for gene delivery according to claim 1, wherein the nanoparticle has a size of 500 nm or less.

7. The nanoparticle for gene delivery according to claim 1, wherein the anionic polymer conjugated via a disulfide bond with the bile acid or bile acid derivative and the nucleic acid molecule encoding a gene are bonded to each other at a molar ratio of 1:1 to 1:200.

8. The nanoparticle for gene delivery according to claim 1, wherein an N/P ratio of the nanoparticle is 1 to 200, wherein the N/P ratio means that a number of nitrogen atoms of the anionic polymer conjugated via a disulfide bond with the bile acid or bile acid derivative/a number of phosphate atoms of the nucleic acid molecule encoding a gene.

9. A pharmaceutical composition for treating diabetes, which comprises a nanoparticle for gene delivery as an active ingredient, wherein the nanoparticle comprises: at least one anionic polymer conjugated via a disulfide bond with a bile acid or a bile acid derivative; and a nucleic acid molecule encoding a gene encoding glucagon-like peptide-1 (GLP-1), a gene encoding a GLP-1 variant, a gene encoding a GLP-1 derivative, a gene encoding a GLP-1 agonist, a gene encoding liraglutide, or a gene encoding exendin-4,
    wherein the bile acid or bile acid derivative is selected from the group consisting of deoxycholic acid, taurodeoxycholic acid, taurocholic acid (TCA), glycocholic acid, and glycochenodeoxycholic acid, and wherein the conjugated bile acid or bile acid derivative is located on the surface of the nanoparticle, wherein the anionic polymer is selected from the group consisting of heparin, hyaluronic acid, and chondroitin sulfate, wherein the nucleic acid molecule encoding a gene is encapsulated in a cationic polymer due to electrostatic interaction, and wherein the cationic polymer is selected from the group consisting of chitosan, glycol chitosan, protamine, poly-L-lysine (PLL), and polyamidoamine (PAMAM).

10. The pharmaceutical composition of claim 9, wherein the pharmaceutical composition is for oral administration.

* * * * *

SEQUENCE LISTING

```
<160> NUMBER OF SEQ ID NOS: 1

<210> SEQ ID NO 1
<211> LENGTH: 4755
<212> TYPE: DNA
<213> ORGANISM: Artificial Sequence
<220> FEATURE:
<223> OTHER INFORMATION: GLP-1 cDNA

<400> SEQUENCE: 1
ggtgggtttc atcgggtggg cccagcggga cagggccggg tgaaattagg gaggggctg      60 ggctggggcg caatggaggc cgagccaatc ccggactcct caatgccagc aaagcttctg     120
gcgccgcccc gtctgaacct ggagcggctg ggaggatccc cctcccagga gaagccgagg     180
accccaggat gctgcagaat cagtgagagg tgcgtaaggc caaacccat tccccggacc      240 ccgctagcac ttcaccacct ggctcagtga tcaaggggtc atgacctctc tttgctgggg     300
ttatcgagaa gtggcaattt tataatagtt actgaaactt acaaagaggt tctggtgccc     360
agagacactt ggggtcatct agggatcaga ggccatgcaa ttccatgtct ctgggctga     420 tgtaggcact ccccagggat catccagggg ttatggaggg caactcaata ataatgaaaa     480
tgataaaaat cgtaatcata ttatggcaag ccagcggcgt ggtggcgcgt gcctgtaagt     540
cccagctact cgggaggctg aggcggaagg atcggtcgag cccaggagtt ctaggctgca    600
ctgagtcctg atcacgcccc tgcactccag gcggggtac agagtgaggc tcggtctcta     660
aaagaaacac aaagaaaaaa agtaacctt ttctcgatcc tgcagccaga ggcttgatat     720
cctgcctcgg tcacctaggg cggtccctgc ctgggtgatc tacgggtgcc gtaagggggtt   780 gattgatgtg gagggctggg cgtgcctggg aggcccacag tgggcgaggt gagttgcaat     840
tactgcaact cttaaaccctt ccacccagag ttagaaatga ctgaacctca ggtgggggtgt    900 gtagcctgtc caagggtaca caaagagccg gcccaagttg gaaccccctg gccggctaaa     960
cccaggagtc acccaagaaa acgtgacccc actgcccttc tccccaggtc cctctggcct    1020
gcatgccagg agtcggtcac cgccctgtgc ttcctccaag agacagtgga gaggctgggt    1080
cagtcccctg cccaggacac cccggtcctg gggccttgct gggacccgat ggctctgggg    1140
actcagggcc gcctgctgct ggacagggat tccaaggaca cacagaccag gatcagccaa    1200
aagggccgcc gtctgcagcc cccggggact ccctcggccc cacccagag aaggccccgg     1260 aaacagctga acccctgccg gggcaccgag agagtggacc ctgggttcga gggggtgact     1320
ctgaagtttc agataaagcc ggactccagc ctgcagatca tccccacgta caggtagggg     1380
```

```
ccggctgggg ccaggccgcc ctttctccca gttacaacgc aaacaccagt gtgggaggta    1440 gggtgctct ctggcgtcgg tgtggaccct cacctgtgct ctacgttaca cgtggcccag     1500
tctctggttg acaacttgag ctggtgccag atacagtcct gccgctcctg actcagtggc    1560
tccccactcc caatgtgaga cctggtctct ttaggaatca ggcctggcct tgcttaggct    1620
gcagctgcgg ctgcggtgat ttttcccaat aatgctaaca gctactattt gttggtagtg    1680
acaacaataa gaggttaaca ggcagtattt tatgtgtatg ggctcattca aaagcctggg    1740
gaggccgggc acagtggctc acgcctataa tcccatcact ttgggaggcc aaggcgagca    1800
gatcacctga agtcaggagt ttgagatcag cctggccaac atagtgaaac ccatgtcta    1860 ctaaaaatac aaaaaattag ctgggcgttg tagtgggtgc ctgtaatccc agctgctcag    1920
gaggctgagg caggagaatc gcttgaactc aggaggtgaa gtcttcagta agcagagata    1980
gcgccacctc actccagcct gagccacaga gtgggactca gtctcaaaaa aaaaaaaaaa    2040
actagctggg aatggtaatg ggcacctgta atcccagcta cttgggaggc tgaggcagga    2100
gaatcgcttg aacccaggag gtggaggttg cactgagcag agatggcacc actgcactcc    2160
agcctgggtg acagagcaag actccatccc cttaaaaaaa aaaaaaaaaa agctttggga    2220
agctgggcct ggtggctcac acctgtaatc ccagcacttt gggaggccaa ggtgggagga    2280
ttgcatgagc ccaggagttc aagaccagcc tgggcaacat agtatgaccc ccagctctaa    2340
tttttaccta tttattgtta ttataaaaat tataattatg acttttttaa tcatgccgcc    2400
aaaacaatat tttttttttt ttttgagatg gagttgcact ctgtcgttca ggctggagtg    2460
caatgacaca atctcggctc actgcaacct ctgcctcccg gattcaaacg attctcctgc    2520
ctcagcctct ggagtagctg ggattacagg tgcctgctac cacgcctggc taattttgt    2580 attttagta gagatggggt tttgccatgt tggccgggat ggtctcgatc tcttgacctc    2640
aggtgatcca tctgccttgc cctcccaaag tgttgggatt acaggagtga gccgccacca    2700
tgcctggctg ctttttttg cttttgtttg tttgtttgtt tttgagacag ggtcttgctc    2760
tgtcacccag ggtggagtgc agtggcgcaa tcatggctca ctgcagcctg acctcccag    2820 gcccaagcca tcctccctcc tcagcctccc aactagctgg gagtgcaggc ctgtaccacc    2880
actcctggct attttttttg tttgtagaga cggggtctcc ctatattgcc cagactccca    2940 tctctttta aaatcaata atcaaattt tcaaagaaaa aaaaactgtt gtattgggaa       3000
gcccatttta cagatgagga aactgaggca cagagtagga gataatgtgt ccaggctcac    3060
acagcaagga catggagaac tgggattgga acctggcagg ctgtccctgt gcttactatt    3120
tttcaaataa taataataat aattaggtcg ggcacggtag ctcatgcctg taatccctgc    3180
actttgggag gccgaggtgg gtggatcact tgaggtcagg agttcgagac cagcctggcc    3240
aacatggtga aaccccgtct gtactaaaaa tacaaaaatt agctgggcgt ggtgtcgcgc    3300
gcctgtagtc ccagctgctt gggaggctga ggctcaagaa ttgcttgaac ccggaggtg    3360 gaggttgtag tgagctgaga tgacaccact acactccagc ctgggcaaca gagcgagact    3420
ccatctgcaa aaataataat aataataata ataatattac taatgagagg caaagccagg    3480
ccattcagat attagttgcc tcctcggggg atggctgata ccttgatact aaatcttcat    3540
ttcggagggc tgttggggac aagctacaga tcccccccag tgctaatacc ttgtctgccc    3600
cacagcctgc cctgcagtag ccgttctcag gaatccctg cagatgctgt tgggggccct    3660
gcagcccacc caggaggcac cgaggcccac tcagcaggca gcgaggccct gggtgagtcc    3720
tgaaaaccca agagctataa atattttggg ggccaatttc ctgtcttccc tgcctttctc    3780
```

```
cctgccccc  ccttctccat  cttgcttccc  catttagagc  cctcagggag  gagtcgcagc  3840
acccccctcc  acttgggctg  agtcaccccc  accccagct   tcctcctctg  cggaatgctg  3900
ccatctgtct  cccttcctgg  ctttgctgtg  gcttagagct  ggcaactccc  agggctgatc  3960
cagagctagg  tggggccttt  actgagaccc  cacaaaatg   cccgactccg  cacaggcatc  4020
ccgagctcac  atgcttggcc  tctgacccct  gcctttgac   ctctgaccct  tcagagcccc  4080
ggcgctgtgc  ttcctgtcgg  acccagagga  ccccgctctg  gagagacgct  gaagatggga  4140
cccctctctg  caacgcctgt  gggatcaggt  ccttagaatg  gaggagggag  ttggggcggg  4200 ggtcccaaa   tcagtccacg  tgtaaccagg  atggcctgtg  gggaaagcaa  aaagcaaaac  4260
acctacctct  tgggaaaagt  ggtttccttg  tggcggtttc  cgggccccca  ctgcatccta  4320
aatggcagtt  tcttgtcccc  caaccctagg  tacaagaaat  acggcactcg  ctgctccagc  4380
tgctggctgg  tgcccaggaa  aaatgtccag  cccaagaggc  tatgtggcag  atgtggagtg  4440
tccctggacc  ccattcagga  aggttaaacc  cagcttcacc  ctgctgagct  gctgcttctg  4500
cctccgtttc  accagtggga  gaatgggcag  aagcagctct  cctaggagga  ttggggaaag  4560
agccggcctg  cctcctctct  gccatctcca  gattcaagga  tcccggggga  agacccaggc  4620
ctcaggtggc  agagcctgct  aggggtcacc  agcccttct   ccagtcagcc  ttggccgagg  4680 cccctcagg   agacgctctc  aggaaggatg  agcattgtta  cagcagggac  aataaagtac  4740
agagatatgc  cgaga                                                        4755
```